(12) United States Patent
Perets et al.

(10) Patent No.: US 11,369,398 B2
(45) Date of Patent: Jun. 28, 2022

(54) HYBRID LASER CUTTER

(71) Applicant: TAG DREAM MEDICAL LTD., Yokne'am Illit (IL)

(72) Inventors: Yuval Perets, Moshav Beit Shearim (IL); Yaron Tal, Tel Mond (IL); Dan Michael, Moshav Beit Shearim (IL); Ran Weisman, Kfar Vradim (IL); Hagay Sitry, Kibbutz Gesher HaZiv (IL); Hagay Botansky, Haifa (IL); Yehuda Ben Ami, Rosh Haayin (IL); Zachary Shane Sacks, Modiin (IL); Dan Nabel, Kiryat Tivon (IL)

(73) Assignee: TAG DREAM MEDICAL LTD., Yokne'am Illit (IL)

(*) Notice: Subject to any disclaimer, the term of this patent is extended or adjusted under 35 U.S.C. 154(b) by 0 days.

(21) Appl. No.: 17/405,617

(22) Filed: Aug. 18, 2021

(65) Prior Publication Data
US 2022/0054193 A1 Feb. 24, 2022

Related U.S. Application Data

(60) Provisional application No. 63/067,368, filed on Aug. 19, 2020.

(51) Int. Cl.
*A61B 18/20* (2006.01)
*A61B 18/22* (2006.01)
(Continued)

(52) U.S. Cl.
CPC .......... *A61B 17/295* (2013.01); *A61B 18/201* (2013.01); *A61B 18/22* (2013.01);
(Continued)

(58) Field of Classification Search
CPC ..... A61B 17/295; A61B 18/201; A61B 18/22; A61B 2018/2272; A61B 2018/2035; A61B 2018/202
See application file for complete search history.

(56) References Cited

U.S. PATENT DOCUMENTS

| 4,046,149 A | 9/1977 | Komiya |
| 4,209,017 A | 6/1980 | Shaw |

(Continued)

FOREIGN PATENT DOCUMENTS

| CN | 106966348 | 1/2019 |
| DE | 2646029 | 4/1978 |

(Continued)

OTHER PUBLICATIONS

Vlaisavljevich, Eli, et al. "Effects of thermal preconditioning on tissue susceptibility to histotripsy." Ultrasound in medicine & biology 41.11 (2015): 2938-2954.

(Continued)

*Primary Examiner* — Gary Jackson
*Assistant Examiner* — Zahed Kabir
(74) *Attorney, Agent, or Firm* — Sughrue Mion, PLLC

(57) ABSTRACT

A tool has a handle and an elongate shaft that extends distally from the handle. A distal portion of the shaft is inserted into a subject during a surgical procedure. An optical fiber delivers laser energy to a tip at the distal portion of the shaft. The tip includes a mechanical cutting mechanism including a moving part that absorbs the laser energy, thermally conducts the absorbed energy to tissue that is disposed between the moving part and another part, and moves with respect to the other part in order to cut tissue that is disposed between the parts using a mechanical force that is lower than a mechanical force that would be required to (Continued)

cut the tissue in the absence of the laser energy. Other embodiments are also described.

20 Claims, 23 Drawing Sheets

(51) Int. Cl.
*A61B 17/295* (2006.01)
*A61B 18/00* (2006.01)
*A61B 17/00* (2006.01)
*A61B 17/29* (2006.01)

(52) U.S. Cl.
CPC ............... *A61B 2017/0088* (2013.01); *A61B 2017/00353* (2013.01); *A61B 2017/00367* (2013.01); *A61B 2017/00831* (2013.01); *A61B 2017/2905* (2013.01); *A61B 2018/00095* (2013.01); *A61B 2018/00601* (2013.01); *A61B 2018/00607* (2013.01); *A61B 2018/202* (2013.01); *A61B 2018/2035* (2013.01); *A61B 2018/225* (2013.01); *A61B 2018/2244* (2013.01); *A61B 2018/2272* (2013.01)

(56) References Cited

U.S. PATENT DOCUMENTS

| | | | |
|---|---|---|---|
| 4,273,127 | A | 6/1981 | Auth et al. |
| 4,509,517 | A | 4/1985 | Zibelin |
| 4,627,435 | A | 12/1986 | Hoskin |
| 4,736,743 | A | 4/1988 | Daikuzono |
| 4,856,518 | A | 8/1989 | McFadden |
| 5,037,421 | A | 8/1991 | Boutacoff et al. |
| 5,154,708 | A | 10/1992 | Long et al. |
| 5,207,673 | A | 5/1993 | Ebling et al. |
| 5,342,358 | A | 8/1994 | Daikuzono |
| 5,352,221 | A | 10/1994 | Fumich |
| 5,366,456 | A | 11/1994 | Rink et al. |
| 5,472,017 | A | 12/1995 | Kovalcheck |
| 5,540,676 | A | 7/1996 | Freiberg |
| 5,766,196 | A | 6/1998 | Griffiths |
| 5,810,809 | A | 9/1998 | Rydell |
| 6,059,776 | A * | 5/2000 | Gatto ............... A61B 17/295 |
| | | | 606/13 |
| 6,071,281 | A | 6/2000 | Burnside et al. |
| 6,099,514 | A | 8/2000 | Sharkey et al. |
| 6,132,468 | A | 10/2000 | Mansmann |
| 6,254,600 | B1 | 7/2001 | Willink et al. |
| 6,267,760 | B1 | 7/2001 | Swanson |
| 6,383,179 | B1 | 5/2002 | Neuberger |
| 6,511,487 | B1 | 1/2003 | Oren et al. |
| 6,533,749 | B1 | 3/2003 | Mitusina et al. |
| 6,786,905 | B2 | 9/2004 | Swanson et al. |
| 7,052,495 | B2 | 5/2006 | Smith |
| 7,167,622 | B2 | 1/2007 | Temelkuran et al. |
| 7,211,080 | B2 | 5/2007 | Treat et al. |
| 7,220,261 | B2 | 5/2007 | Truckai et al. |
| 7,294,139 | B1 | 11/2007 | Gengler |
| 7,393,351 | B2 | 7/2008 | Woloszko et al. |
| 7,608,091 | B2 | 10/2009 | Goldfarb et al. |
| 7,670,284 | B2 | 3/2010 | Padget et al. |
| 7,819,863 | B2 | 10/2010 | Eggers et al. |
| 7,883,519 | B2 | 2/2011 | Oren et al. |
| 8,137,263 | B2 | 3/2012 | Marescaux et al. |
| 8,430,881 | B2 | 4/2013 | Bleich et al. |
| 8,517,239 | B2 | 8/2013 | Scheib et al. |
| 8,685,020 | B2 | 4/2014 | Weizman et al. |
| 8,968,312 | B2 | 3/2015 | Marczyk et al. |
| 9,603,656 | B1 | 3/2017 | Germain et al. |
| 9,636,163 | B2 | 5/2017 | Lau et al. |
| 9,757,194 | B2 | 9/2017 | Werneth et al. |
| 9,980,737 | B2 | 5/2018 | Thommen et al. |
| 10,321,927 | B2 | 6/2019 | Hinman |
| 10,327,842 | B2 | 6/2019 | Germain et al. |
| 10,524,779 | B2 | 1/2020 | Murillo et al. |
| 10,753,439 | B2 | 8/2020 | Awtar |
| 2005/0222598 | A1 | 10/2005 | Ho et al. |
| 2006/0074407 | A1 | 4/2006 | Padget et al. |
| 2008/0161809 | A1 | 7/2008 | Schmitz et al. |
| 2009/0182314 | A1* | 7/2009 | Eliachar ............... A61B 18/24 |
| | | | 606/15 |
| 2011/0009863 | A1 | 1/2011 | Marczyk et al. |
| 2011/0009867 | A1 | 1/2011 | Oren et al. |
| 2011/0087202 | A1* | 4/2011 | Lewinsky ............ A61N 5/0603 |
| | | | 606/14 |
| 2011/0301601 | A1 | 12/2011 | Garrison et al. |
| 2013/0253489 | A1 | 9/2013 | Nau, Jr. et al. |
| 2014/0031800 | A1* | 1/2014 | Ben Oren ............ A61B 18/22 |
| | | | 606/7 |
| 2014/0066911 | A1* | 3/2014 | Nau, Jr. ............... A61B 18/201 |
| | | | 606/8 |
| 2014/0288541 | A1 | 9/2014 | Eshkol et al. |
| 2016/0074028 | A1* | 3/2016 | Castro ............... A61B 18/1442 |
| | | | 606/130 |
| 2016/0157928 | A1 | 6/2016 | Eshkol et al. |
| 2016/0206336 | A1 | 7/2016 | Frushour |
| 2017/0065346 | A1 | 3/2017 | Weisberg et al. |
| 2017/0245933 | A1 | 8/2017 | Graham et al. |
| 2017/0251907 | A1 | 9/2017 | Piskun et al. |
| 2017/0281256 | A1 | 10/2017 | Slatkine et al. |
| 2018/0235600 | A1 | 8/2018 | Nachmias et al. |
| 2018/0242962 | A1 | 8/2018 | Walen et al. |
| 2018/0242968 | A1 | 8/2018 | Mirochinik et al. |
| 2018/0263649 | A1 | 9/2018 | Germain et al. |
| 2018/0296272 | A1* | 10/2018 | Nau, Jr ............... A61B 17/29 |
| 2019/0083121 | A1 | 3/2019 | Benamou et al. |
| 2019/0231179 | A1 | 8/2019 | Hansen et al. |
| 2019/0298338 | A1* | 10/2019 | Vendely ............... A61B 17/068 |
| 2019/0328434 | A1 | 10/2019 | Slocum et al. |
| 2020/0178994 | A1 | 6/2020 | Honegger |

FOREIGN PATENT DOCUMENTS

| | | |
|---|---|---|
| EP | 1878389 | 1/2008 |
| EP | 2785288 | 5/2017 |
| EP | 2211732 | 5/2018 |
| EP | 2588010 | 10/2019 |
| WO | 1993/025267 | 12/1993 |
| WO | 1994/010897 | 5/1994 |
| WO | 2011/082074 | 7/2011 |
| WO | 2013/114376 | 8/2013 |
| WO | 2014/089198 | 6/2014 |
| WO | 2016/001061 | 1/2016 |

OTHER PUBLICATIONS

Rizzuto, Antonia, et al. "The twin forceps: a new instrument for SILS." BioMed research international 2015 (2015).
Jung, Woonggyu, et al. "Numerical analysis of gradient index lens-based optical coherence tomography imaging probes." Journal of biomedical optics 15.6 (2010): 066027.
Alma Surgical _ Vasculife™ _ Varicose Vein Solution (https://www.almalasers.com/alma-products/vasculife/ accessed Jul. 2019).
Alma VascuLife_b2b_WEB-1 (Alma lasers, 2015).
Helicut Burrs _ Smith & Nephew UK (https://www.smith-nephew.com/uk/products/sports-medicine/resection/blades-and-burrs/helicut/ accessed Jun. 2020).
U.S. Appl. No. 61/678,753, filed Aug. 2, 2012.
U.S. Appl. No. 61/592,602, filed Jan. 31, 2012.
Design and Characterization of a Debriding Tool in Robot-Assisted (Alambeigi et al., May 2016 DOI: 10.1109/ICRA.2016.7487787).
Fiber Optic Medical Solutions—OFS Optics EMEA (https://www.ofsoptics.com/medical/ accessed Jul. 2019).
Medical and Health Sciences, vol. XVIII—screenshot from Hanninen, Osmo Otto Paivio, et al., eds. Medical and Health Sciences—vol. VIII. EOLSS Publications, 2010.
Medical devices—Products for laser medicine by LEONI-LEONI (https://www.leoni-fiber-optics.com/en/products-and-services/assemblies/medical-devices/ accessed Jul. 2019).

(56) References Cited

OTHER PUBLICATIONS

Optical Probe Tips—Doric Lenses (https://doriclenses.com/life-sciences/optical-fiber-probe/863-optica accessed Jul. 2019).
Steerable-Punch-leaflet (Surge-on Medical B.V., 2020).
U.S. Appl. No. 63/067,368, filed Aug. 19, 2020.
An International Search Report and a Written Opinion both dated Nov. 10, 2021, which issued during the prosecution of Applicant's PCT/IL2021/051004.

\* cited by examiner

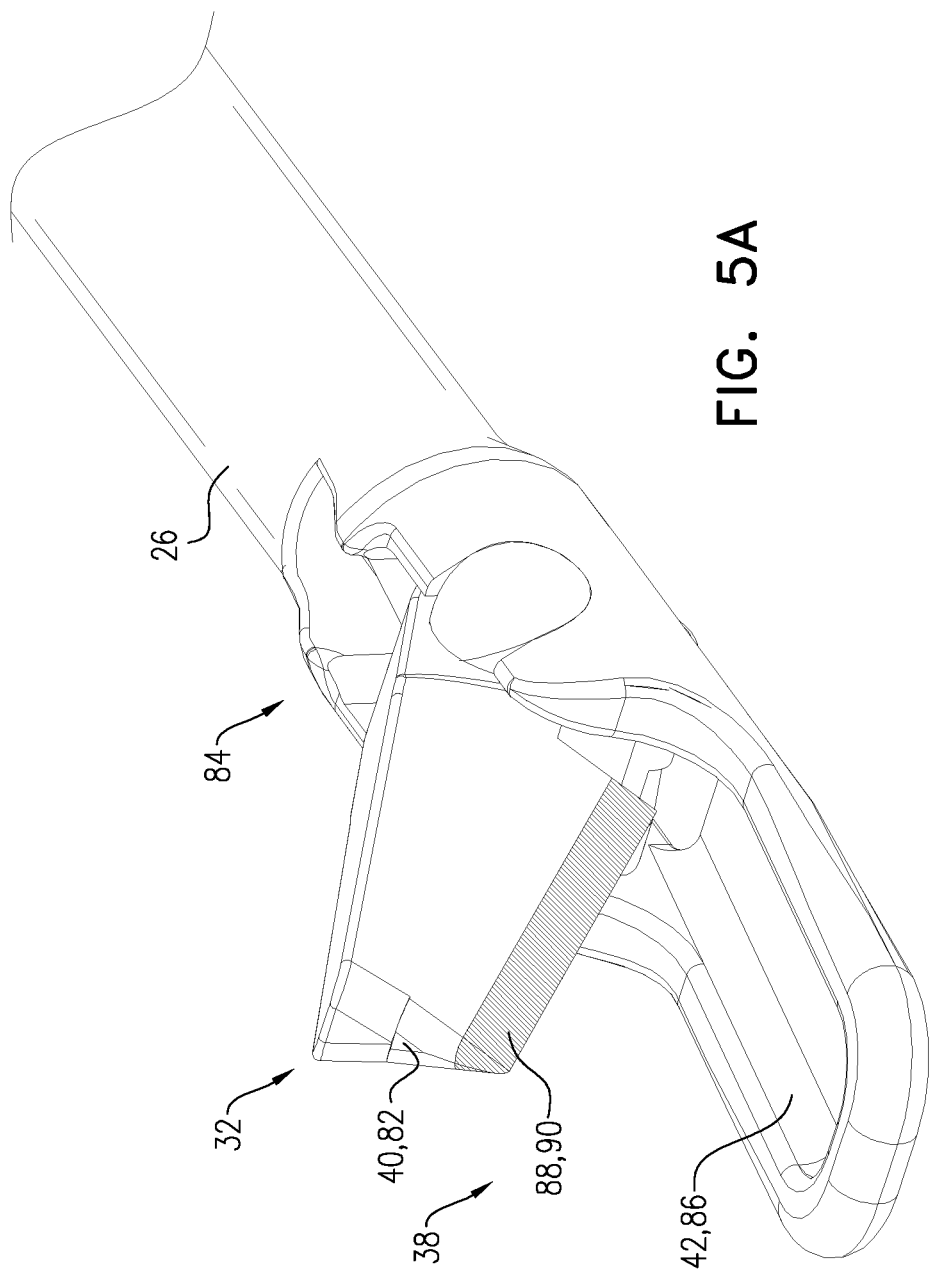

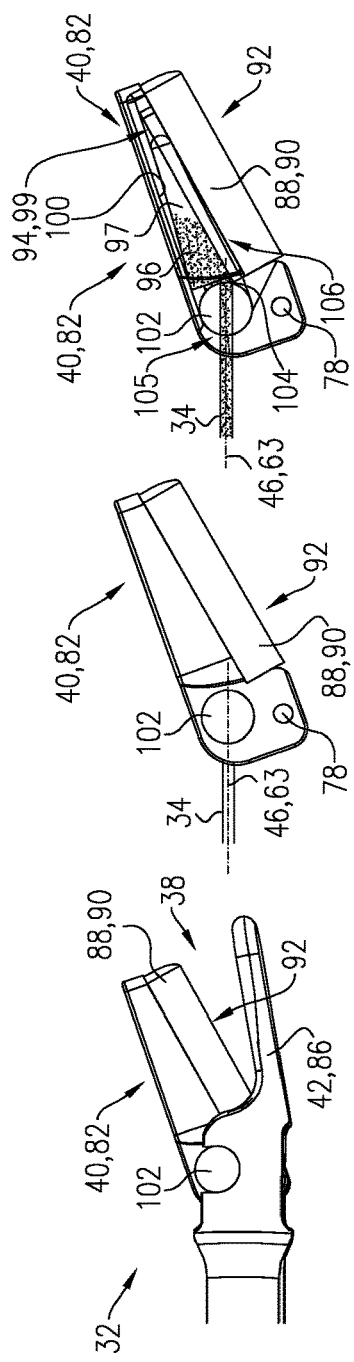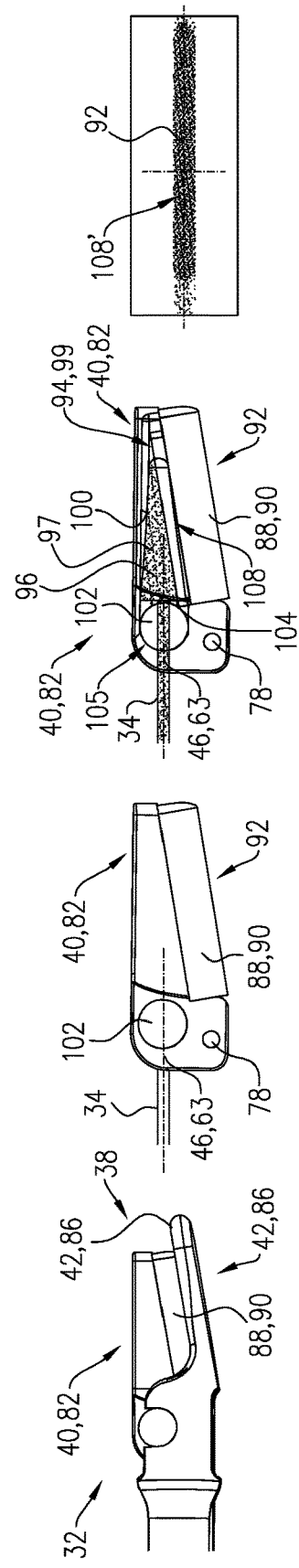

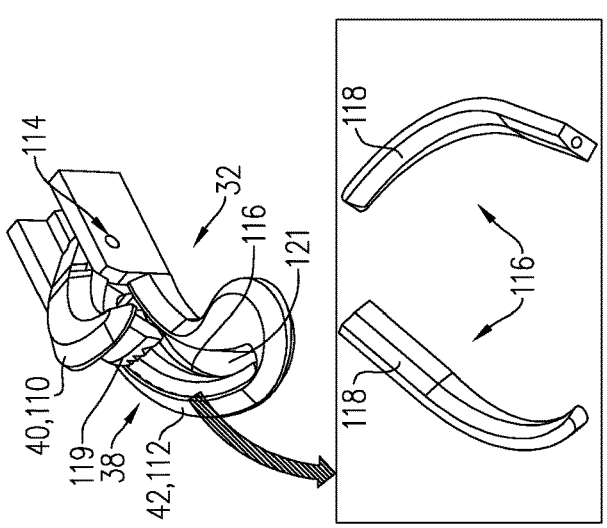
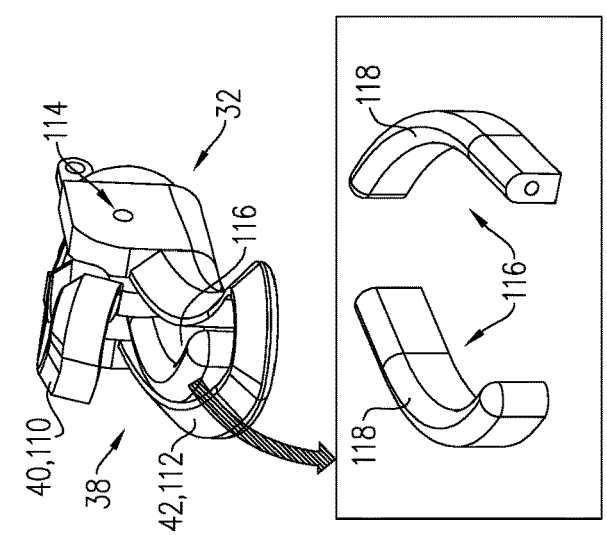
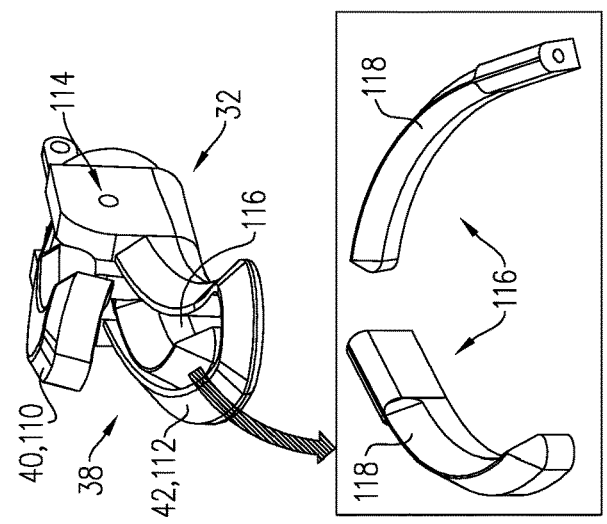
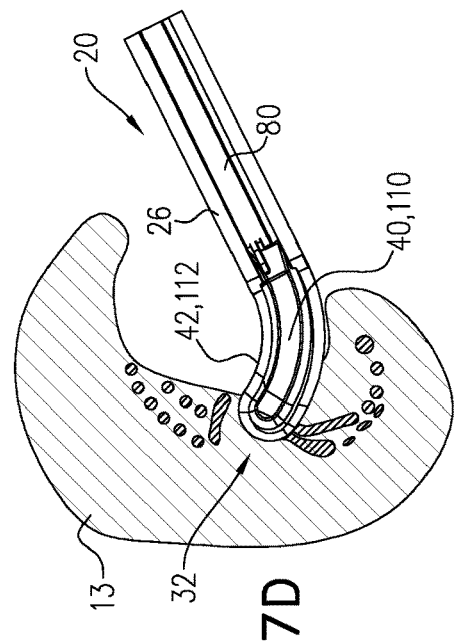
FIG. 7A
FIG. 7B
FIG. 7C
FIG. 7D

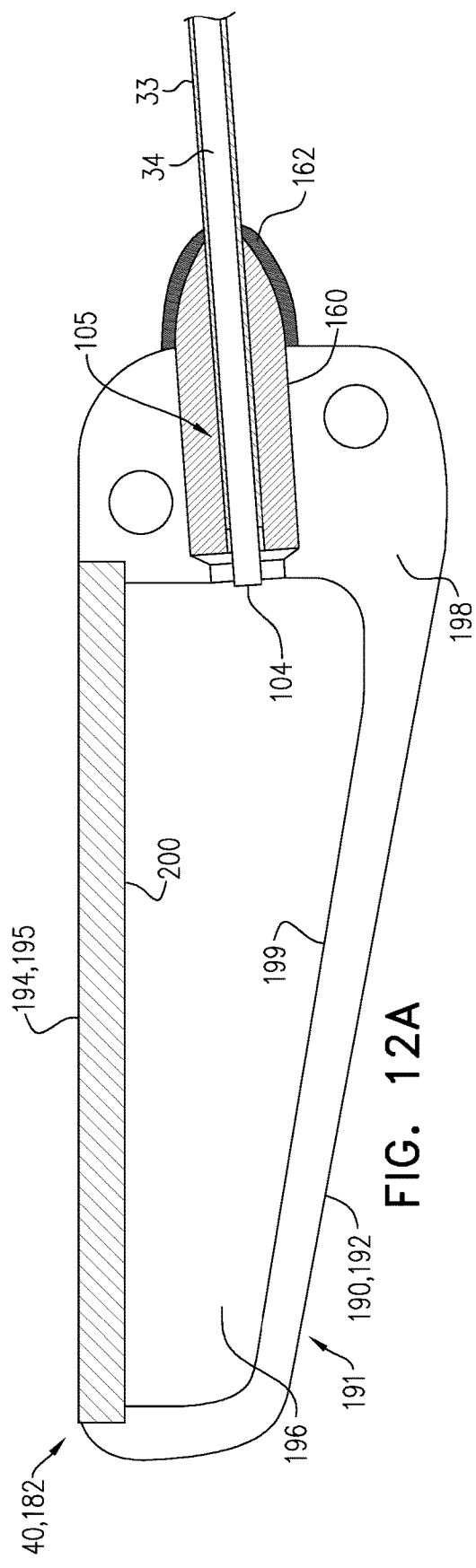
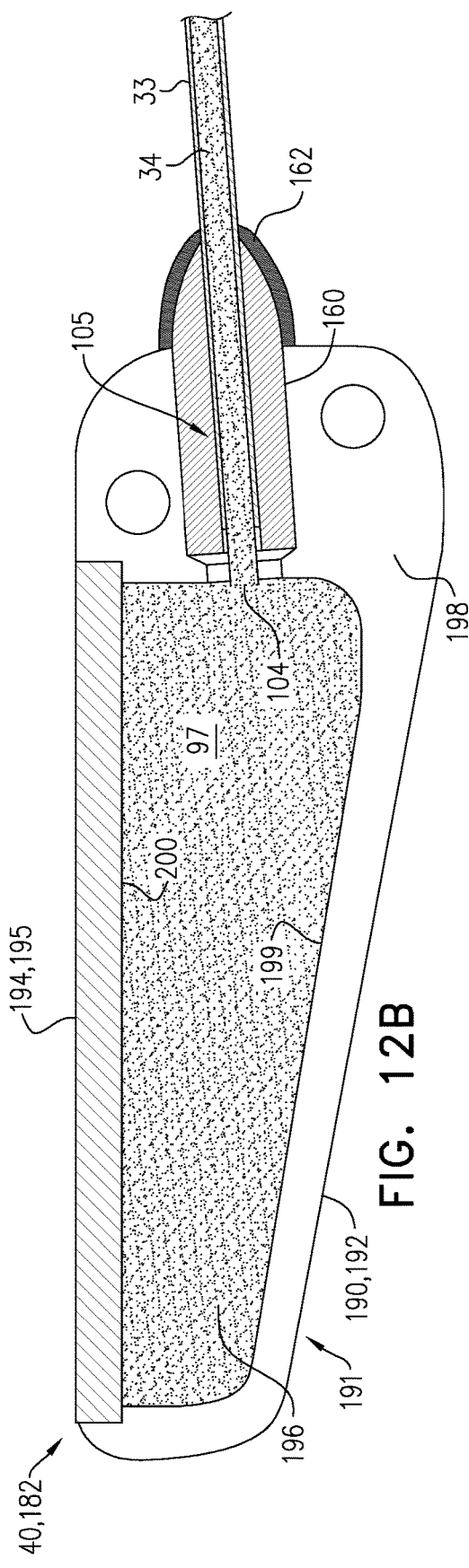

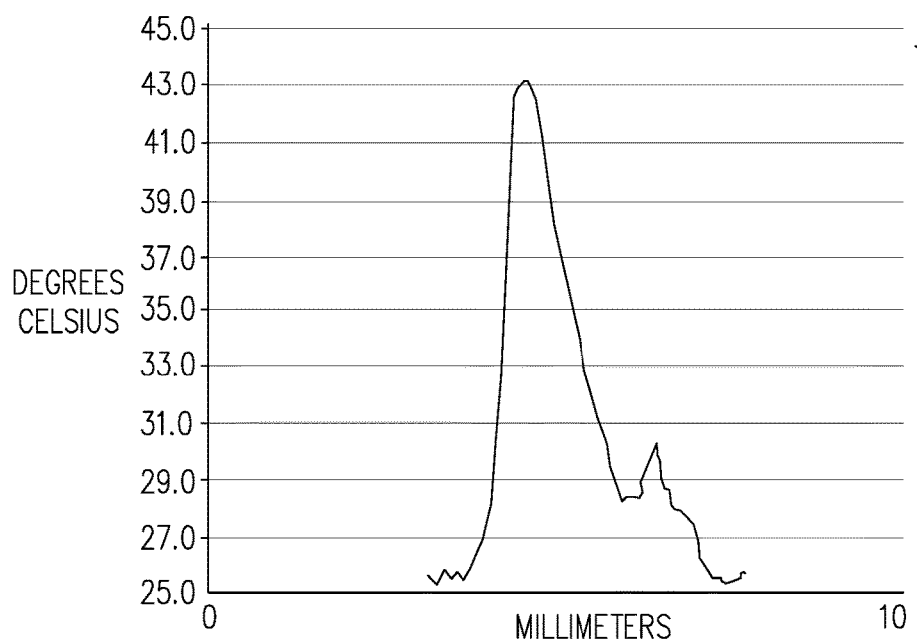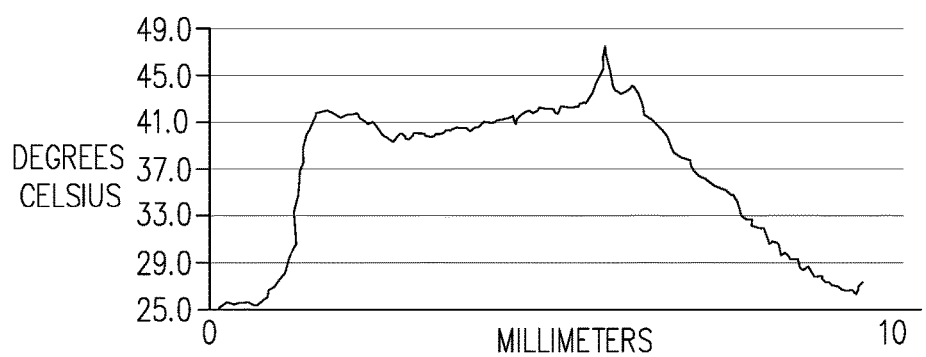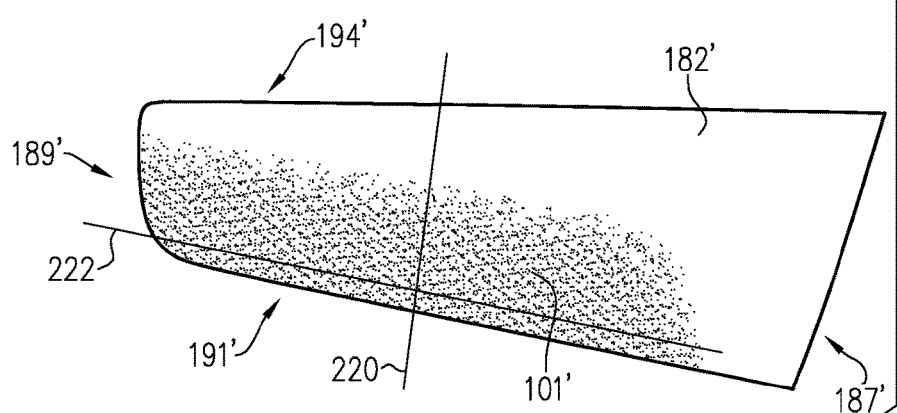
FIG. 12C

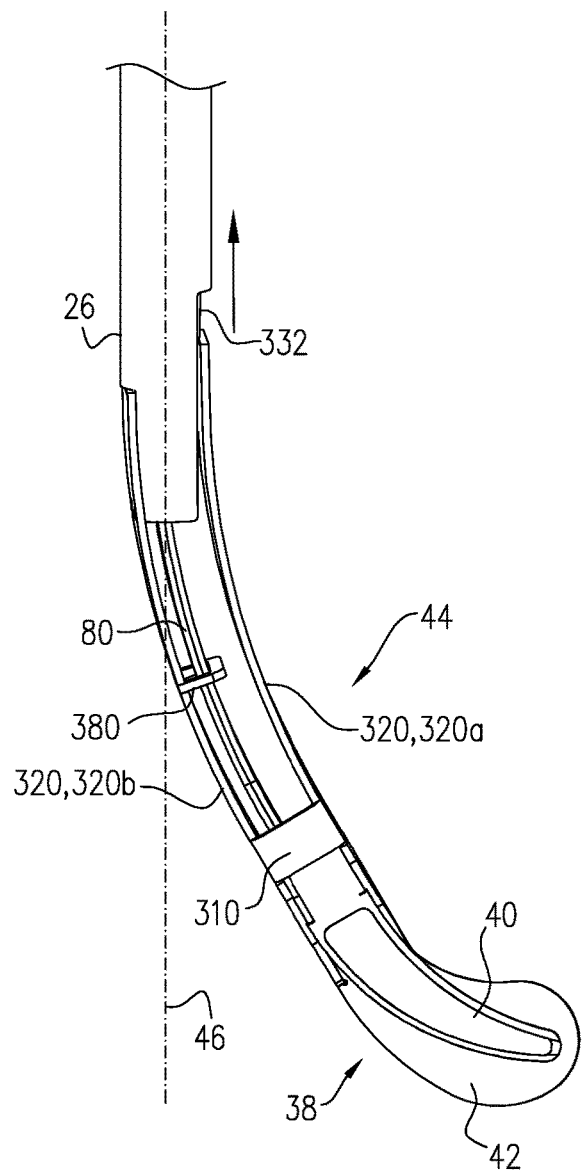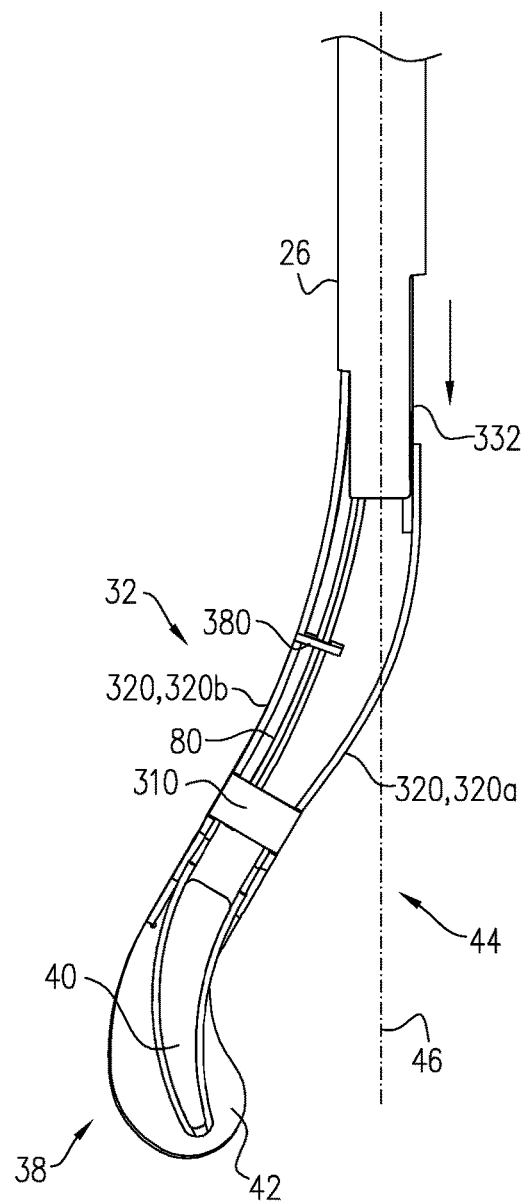
FIG. 14C
FIG. 14D

HYBRID LASER CUTTER

CROSS-REFERENCE TO RELATED APPLICATIONS

The present application claims priority from U.S. Provisional Application 63/067,368, filed Aug. 19, 2020, entitled, "HYBRID LASER CUTTER," which is assigned to the assignee of the present application and is incorporated herein by reference.

This application is related to an international patent application to Perets et al., entitled, "HYBRID LASER CUTTER," filed on even date herewith.

FIELD OF THE INVENTION

The present invention relates generally to surgical tools, and more particularly to minimally invasive surgical tools.

BACKGROUND

A common surgical tool for tissue cutting in minimally invasive surgical procedures is a tool having a hinged handle that utilizes mechanical force for interacting with various types of tissues, e.g., cutting, biting, grasping, or punching out various types of tissues. These types of tools are often used in arthroscopic surgical procedures, e.g., arthroscopic meniscectomy or an anterior cruciate ligament (ACL) procedure, and sometimes used in open surgery, laparoscopic surgery, proctology, and spinal surgery as well. During minimally invasive surgical procedures, radio frequency energy is often used to ablate and coagulate tissue.

SUMMARY OF THE INVENTION

In accordance with some applications of the present invention, a minimally invasive surgical tool is provided that utilizes a hybrid of laser energy and mechanical force. The laser energy generates a photothermal effect that heats the tissue and thereby softens the tissue, allowing a mechanical cutting mechanism of the surgical tool to cut tissue of a subject using a mechanical force that is lower than a mechanical force that would be required to cut the tissue in the absence of the laser energy. Since the tissue being treated may be fairly hard, and often the tissue interaction mechanism (e.g., cutting mechanism, biting mechanism, grasping mechanism, or punching mechanism) is small in order to fit inside a limited space within the subject's body, strong mechanical forces are often used in the tissue interaction mechanism of some conventional minimally invasive tissue surgical tools. To support the strong mechanical forces, these types of conventional surgical tools often have a stiff mechanical structure and large profile diameter. The lower mechanical force enabled by the presence of the laser energy allows the surgical tool described herein to have an overall smaller profile than many existing minimally invasive surgical tools, e.g., cutters, biters, and graspers. The cutting rate of the mechanical cutting mechanism is also typically faster than a cutting rate that it would take to mechanically cut the tissue in the absence of the laser energy, or by using laser energy alone to cut the tissue in the absence of mechanical cutting. For some applications, the laser energy coagulates the cut tissue.

The minimally invasive surgical tool, in accordance with some applications of the present invention, typically has a handle, e.g., a hinged scissors-like handle, at a proximal end of the tool and an elongate shaft extending in a distal direction from the handle. A tip is disposed at a distal portion of the shaft and is sized and shaped to be inserted into a subject during a surgical procedure and to contact tissue of the subject. The tip typically includes a mechanical cutting mechanism that has a moving part that moves with respect to another part in order to cut tissue of the subject that is disposed between the two parts. The laser energy is delivered to the tip by an optical fiber.

For some applications, the photothermal effect is achieved by directly irradiating the tissue that is disposed between the two parts of the mechanical cutting mechanism, e.g., by emitting laser energy from the optical fiber to the tissue.

For some applications, the photothermal effect is achieved by using laser energy to heat at least a portion of the mechanical cutting mechanism. For example, the portion of the mechanical cutting mechanism may be sufficiently heated by the laser energy in order to vaporize the tissue with which it comes into contact (e.g., the cut tissue). Typically for such applications, tissue immediately adjacent the cut tissue is coagulated. By heating a limited portion (e.g., a lower edge) of the mechanical cutting mechanism, the heat-affected zone of the tissue is limited.

Nd:YAG lasers, while often expensive, are conventionally used in surgical procedures to ablate or vaporize tissue utilizing the photothermal effect. The photothermal effect caused by laser irradiation of tissue can also cauterize and seal small blood vessels in the tissue. Due to laser irradiation of tissue being a non-contact form of tissue treatment, a physician does not receive any tactile feedback from the tissue and it can sometimes be challenging to judge the depth of tissue ablation.

Unlike with the use of many conventional lasers for tissue cutting, which generally operate in a point-and-shoot manner, utilizing a hybrid system of laser energy and mechanical force, with the laser energy being integrated within the mechanical device, allows the surgeon to locate, visualize, and be in tactile control of the target tissue location before activating the laser energy and making the actual cut. As described above, the combination of laser energy and mechanical cutting allows the mechanical cutting force to be lower, the cutting rate to be faster, and the device to have a smaller profile.

Furthermore, with many conventional lasers for tissue cutting, there is a narrow process window that enables the tissue to be exposed to a specific energy density; if the energy density is lower than a photothermal threshold there would be no effect or only a small amount of heating, whereas if the energy density is too high, excessive heat may be generated leading to tissue carbonization. As used herein, the term "process window" refers to the combination of parameters of the laser energy for any given tissue in order to effect the desired tissue treatment while avoiding carbonization. The inventors have realized that by implementing a hybrid system of laser energy and mechanical force, together with laser control using beam delivery optics and management as further described hereinbelow, the process window can be expanded to include lower energy levels than if the tissue cutting were to be done using laser energy alone. Due to the laser energy level being lower than conventional laser tissue cutting, less expensive and simpler-to-use laser diodes or diode pumped solid state lasers may be used, as opposed to the conventional lasers often used for laser surgical procedures, e.g., holmium-doped yttrium aluminum garnet (Ho:YAG) or neodymium-doped yttrium aluminum garnet (Nd:YAG) lasers.

The laser is only used to heat the tissue to a temperature of at least 50 degrees Celsius, e.g., at least 60 and/or less than 65 degrees Celsius (alternatively or additionally between 60+/−5 degrees Celsius and 65+/− degrees Celsius), which is low enough to avoid typically undesired effects on the tissue (e.g., denaturization, dehydration, and/or carbonization), but high enough to allow the mechanical cutting of the tissue to use less force and to coagulate the cut tissue. The result is a fast, clean cut with simultaneous coagulation that requires between 25 percent and 80 percent less mechanical force than would be required to cut the tissue by mechanical force alone, without the laser energy.

Various electromagnetic and acoustic energy delivery sources are known to be used in surgical tissue ablation or removal, including Radio Frequency (RF) current flow within tissue, high intensity focused ultrasound (HIFU) tissue interactions and microwave energy absorption in tissue. In general, at high intensities, these energy sources generate a thermal effect that can vaporize tissue. During this type of thermally-mediated ablation there may be a relatively large heat affected zone in which tissue that is adjacent to the targeted ablation site is affected as well. RF energy is used in order to generate a plasma spark for cutting, ablation, and coagulation; this method typically generates large amount of heat and may leave a heat affected zone of hundreds of micrometers. Carbonization of the tissue may also occur. In some conventional minimally invasive surgical procedures, after mechanically cutting the tissue, a surgeon sometimes removes the minimally invasive mechanical device from the subject's body and then inserts an RF tool in order to coagulate the tissue that was cut.

In contrast to coagulation performed by RF energy (which can leave a heat affected zone of 0.6-2 mm and may significantly heat the fluids around the treated area), utilizing laser energy integrated into the mechanical device, as described herein, leaves a substantially smaller heat-affected zone than coagulation using RF energy, e.g., approximately ten times smaller (e.g., tens of microns compared to hundreds of microns) surrounding the target tissue-cutting location, further described hereinbelow.

Often during a conventional minimally invasive surgical procedure that involves cutting tissue, e.g., an arthroscopic surgical procedure, many different mechanical tools, e.g., cutters, biters, and graspers, are used, each with different predefined angles and tip sizes and shapes. Frequently, the entire set of tools is sterilized in between procedures, regardless of whether they were used or not. Additionally, entering and exiting the subject's body with multiple tools during a procedure can sometimes have an undesired effect on surrounding tissue.

Advantageously, for some applications, the tip of the tool can be configured to articulate with respect to the shaft of the tool, such that multiple orientations and angles of the tip with respect to the shaft may be achieved (obviating the use of multiple separate tools having different angles and/or orientations of the tip). Often in a conventional minimally invasive surgical tool, such as a cutter, biter, or grasper, the addition of an articulation system for the tip may substantially add to the overall size and profile of the tool. The inventors have realized that due to the laser energy enabling a smaller mechanical cutting force to be used, and thereby an overall smaller device profile, an articulation system may be implemented while keeping the mechanics of the device relatively small and low-profile. For some applications, the articulation capability is provided by a deformable (e.g., plastically deformable) distal portion of the shaft that a surgeon can bend before or during a procedure to whatever orientation is desired. For some applications, the deformation is easily reversible.

There is therefore provided, in accordance with some applications of the present invention, an apparatus for use in a surgical procedure, the apparatus including:
a tool including:
a handle at a proximal end of the tool;
an elongate shaft extending in a distal direction from the handle, the elongate shaft having proximal and distal portions;
a tip disposed at the distal portion of the shaft, the distal portion of the shaft being sized and shaped to be inserted into a subject during a surgical procedure and to contact tissue of the subject; and
an optical fiber configured to deliver laser energy to the tip,
the tip includes a mechanical cutting mechanism including a moving part that:
moves with respect to another part in order to cut tissue of the subject that is disposed between the parts, and
is configured to absorb the laser energy and thermally conduct the absorbed energy to the tissue by contacting the tissue that is disposed between the parts; and
the mechanical cutting mechanism is configured to cut the tissue of the subject using a mechanical force that is lower than a mechanical force that would be required to cut the tissue in the absence of the thermally conducted absorbed energy.

In an application, the apparatus includes a laser configured to generate the laser energy.

In an application, the distal portion of the elongate shaft includes a shape-changing region that is configured to change shape during the surgical procedure.

In an application, the shape-changing region has a bend radius that is less than 30 mm.

In an application, a widest part of the shape-changing region has a cross-section perpendicular to a longitudinal axis of the shape-changing region, the cross-section having a width of less than 3 mm.

In an application, the shape-changing region is configured to change shape under active control by the handle.

In an application, the shape-changing region is configured to change shape more in a first plane than in a second plane perpendicular to the first plane.

In an application, the apparatus includes an actuator that extends distally to the shape-changing region,
the shape-changing region includes a side-plate, the side-plate having a relaxed state and a deflected state, and
the actuator is operatively coupled to the side-plate such that actuation of the side-plate by the actuator causes the side-plate to flex along the first plane, such that the side-plate transitions from the relaxed state to the deflected state.

In an application, the side-plate has a greatest thickness of between 0.1-0.5 mm.

In an application, the greatest thickness of the side-plate is less than 0.3 mm.

In an application:
the side-plate is a first side-plate; and
the shape-changing region includes:
a second side-plate; and
a connecting portion that connects a distal portion of the first side-plate to a distal portion of the second side-plate.

In an application:
the moving part of the mechanical cutting mechanism includes a mechanical cutting blade that is coupled to the tip at a mechanical joint, and
the other part of the mechanical cutting mechanism includes a cutting surface against which the mechanical cutting blade slides as the mechanical cutting blade pivots from an open position to a closed position.

In an application:

the moving part of the mechanical cutting mechanism includes a mechanical cutting blade that is coupled to the tip at a mechanical joint, and the other part of the mechanical cutting mechanism is a tissue-stabilizing base configured to stabilize the tissue disposed between the mechanical cutting blade and the tissue-stabilizing base as the mechanical cutting blade cuts the tissue by pivoting toward the tissue-stabilizing base.

In an application, at least a portion of the mechanical cutting blade is configured to absorb the laser energy and thermally conduct the absorbed energy to the tissue by contacting the tissue that is disposed between the mechanical cutting blade and the tissue-stabilizing base.

In an application, the optical fiber is configured to deliver the laser energy to the tip such that the at least a portion of the mechanical cutting blade coagulates the tissue upon thermally conducting the absorbed energy to the tissue.

In an application, the optical fiber is configured to deliver the laser energy to the tip such that the at least a portion of the mechanical cutting blade vaporizes the tissue upon thermally conducting the absorbed energy to the tissue.

In an application:

the at least a portion of the mechanical cutting blade is a tissue-cutting element of the mechanical cutting blade, the tissue-cutting element (a) having low thermal mass and high thermal conductivity, and (b) having a lower portion defining a lower edge that is configured to face the tissue, and an upper edge opposite the lower edge that faces away from the tissue, the mechanical cutting blade is shaped to define a hollow cavity, the hollow cavity having an internal surface with high reflectivity, the optical fiber is positioned so as to emit the laser energy into the internal cavity, and the internal surface of the hollow cavity is shaped so as to reflect the laser energy toward the lower edge of the tissue-cutting element of the mechanical cutting blade.

In an application:

the internal surface of the hollow cavity with high reflectivity is an internal upper surface of the tissue-cutting element, and the lower portion of the tissue-cutting element defines an internal lower surface of the hollow cavity, and the internal upper surface of the hollow cavity is shaped so as to reflect the laser energy in a direction that is toward:

the internal lower surface of the hollow cavity, and the lower edge of the tissue-cutting element.

In an application, the internal upper surface is smoother than the internal lower surface.

In an application, the internal lower surface is shaped to define a plurality of microperforations.

In an application, the apparatus includes a ceramic sleeve that circumferentially surrounds a distal portion of the optical fiber, at least a portion of the ceramic sleeve being disposed within the tissue-cutting element.

In an application, the apparatus includes an adhesive, the adhesive forming a watertight seal between:

the ceramic sleeve and the tissue-cutting element, and the optical fiber and the ceramic sleeve.

In an application, the internal surface of the hollow cavity is a reflective coating.

In an application:

the internal upper surface of the hollow cavity has a high reflectivity, and the upper edge of the tissue-cutting element of the mechanical cutting blade forms a lower surface of the hollow cavity, and the internal upper surface of the hollow cavity is shaped so as to reflect the laser energy in a direction that is toward both the upper and lower edges of the tissue-cutting element.

In an application, the mechanical cutting blade is configured such that the lower surface of the hollow cavity reflects no more than 30 percent of the laser energy that reaches the lower surface of the hollow cavity.

In an application, the mechanical cutting blade is configured such that, for a same amount of laser energy that reaches the internal upper surface of the hollow cavity and the lower surface of the hollow cavity, the internal upper surface of the hollow cavity reflects at least two times as much of the laser energy.

In an application, the mechanical cutting blade is configured such that, for a same amount of laser energy that reaches the internal upper surface of the hollow cavity and the lower surface of the hollow cavity, the internal upper surface of the hollow cavity reflects at least three times as much of the laser energy.

In an application, the mechanical cutting blade is configured such that the internal upper surface of the hollow cavity reflects at least 85 percent of the laser energy that reaches the internal upper surface.

In an application, the mechanical cutting blade is configured such that the internal upper surface of the hollow cavity reflects at least 90 percent of the laser energy that reaches the internal upper surface.

In an application, the internal upper surface of the hollow cavity has a reflective coating.

In an application, the apparatus includes a pivot, and the mechanical cutting blade is configured to pivot toward the tissue-stabilizing base around the pivot, and a distal end of the optical fiber is disposed within the pivot.

In an application:

the mechanical cutting element has at least two positions as it pivots toward the tissue-stabilizing base, and (a) in a first one of the at least two positions the laser energy is reflected toward a first location along the upper edge of the tissue-cutting element, and (b) in a second one of the at least two positions the laser energy is reflected toward a second location along the upper edge of the tissue-cutting element, distal to the first location.

In an application:

the optical fiber is positioned so as to emit the laser energy into the hollow cavity in a direction that is parallel to a central longitudinal axis of the elongate shaft, and the mechanical cutting blade is configured such that as the mechanical cutting blade pivots, the distal end of the optical fiber remains parallel to the central longitudinal axis of the elongate shaft.

In an application:

the other part of the mechanical cutting mechanism includes a grasper (a) having first and second grasping elements, and (b) configured to grasp tissue of the subject between the first and second grasping elements, and the moving part of the mechanical cutting mechanism is a mechanical cutting blade disposed within the grasper and configured to slide with respect to the grasper to cut the grasped tissue.

In an application:

the first and second grasping elements include a first jaw and a second jaw, respectively, (a) the first and second jaws being coupled to each other at a jaw-hinge, and (b) the grasper being configured to grasp the tissue of the subject between the first and second jaws, and the mechanical cutting blade is disposed within the second jaw and is configured to slide longitudinally with respect to the second jaw to cut the tissue grasped between the first and second jaws.

In an application:

the first and second grasping elements include a first jaw and a second jaw, respectively, (a) the first and second jaws being coupled to each other at a jaw-hinge, and (b) the grasper being configured to grasp the tissue of the subject between the first and second jaws, and the mechanical cutting blade is disposed within the first jaw and is configured to slide longitudinally with respect to the first jaw to cut the tissue grasped between the first and second jaws.

In an application, at least a portion of the mechanical cutting blade is configured to absorb the laser energy and thermally conduct the absorbed energy to the tissue by contacting the tissue that is disposed between the mechanical cutting blade and the grasper.

In an application, the optical fiber is configured to deliver the laser energy to the tip such that the at least a portion of the mechanical cutting blade coagulates the tissue upon thermally conducting the absorbed energy to the tissue.

In an application, the optical fiber is configured to deliver the laser energy to the tip such that the at least a portion of the mechanical cutting blade vaporizes the tissue upon thermally conducting the absorbed energy to the tissue.

In an application, the at least a portion of the mechanical cutting blade has low thermal mass and high thermal conductivity.

In an application, the optical fiber is configured to deliver the laser energy to the tip such that the at least a portion of the moving part coagulates the tissue upon thermally conducting the absorbed laser energy to the tissue.

In an application, the optical fiber is configured to deliver the laser energy to the tip such that the at least a portion of the moving part vaporizes the tissue upon thermally conducting the absorbed energy to the tissue.

In an application:

the at least a portion of the moving part of the mechanical cutting mechanism includes a tissue-cutting element (a) having low thermal mass and high thermal conductivity, and (b) having a lower edge configured to face the tissue and an upper edge opposite the lower edge that faces away from the tissue, the moving part of the mechanical cutting mechanism is shaped to define a hollow cavity, the hollow cavity having an internal surface with high reflectivity, the optical fiber is positioned so as to emit the laser energy into the internal cavity, and the internal surface of the hollow cavity is shaped so as to reflect the laser energy toward the cutting element.

In an application, the internal surface of the hollow cavity is a reflective coating.

In an application:

the internal surface of the hollow cavity with high reflectivity is an internal upper surface with high reflectivity, and the upper edge of the tissue-cutting element of the mechanical cutting blade forms a lower surface of the hollow cavity, and the internal upper surface of the hollow cavity is shaped so as to reflect the laser energy toward the upper edge of the tissue-cutting element of the mechanical cutting blade.

In an application, the internal upper surface of the hollow cavity has a reflective coating.

There is further provided, in accordance with an application of the present invention, a method for use with a tissue of a subject, the method including:

using a tool, the tool including:

an elongate shaft extending distally from a proximal portion to a distal portion, a tip disposed at the distal portion of the shaft, the tip including a mechanical cutting mechanism that includes a first part and a second part, and an optical fiber extending from the proximal portion of the shaft to the tip:

delivering the distal portion of the shaft into the subject, such that tissue of the subject is disposed between the first part and the second part of the mechanical cutting mechanism;

delivering laser energy along the optical fiber, to the tip; and cutting the tissue that is disposed between the first part and the second part by moving the first part with respect to the second part using a mechanical force that is lower than a mechanical force that would be required to cut the tissue in the absence of the laser energy.

There is further provided, in accordance with an application of the present invention, an apparatus for use in a surgical procedure, the apparatus including:

a tool including:

a handle at a proximal end of the tool;

an elongate shaft extending in a distal direction from the handle, the elongate shaft having proximal and distal portions;

a tip disposed at the distal portion of the shaft, the distal portion of the shaft being sized and shaped to be inserted into a subject during a surgical procedure and to contact tissue of the subject; and an optical fiber configured to deliver laser energy to the tip, the tip includes a mechanical cutting mechanism including a moving part that moves with respect to another part in order to cut tissue of the subject that is disposed between the parts, the optical fiber is configured to deliver the laser energy to the tip such that the laser energy leaves the tip and irradiates the tissue that is disposed between the parts, and the mechanical cutting mechanism is configured to cut the tissue of the subject using a mechanical force that is lower than a mechanical force that would be required to cut the tissue in the absence of the laser energy.

In an application, the apparatus includes an optical light guide disposed at least partially within the tip and coupled to a distal end of the optical fiber, the optical light guide configured to direct the laser energy toward the tissue that is disposed between the parts.

In an application, the apparatus includes a laser configured to generate the laser energy.

In an application:

the moving part is a mechanical cutting blade, the other part is a cutting surface, and the optical fiber is configured to deliver the laser energy to the tip such that the laser energy leaves the tip and irradiates the tissue that is disposed between the mechanical cutting blade and the cutting surface.

In an application, the optical fiber is configured to deliver the laser energy to the tip such that the laser energy leaves the tip and heats the tissue that is disposed between the mechanical cutting blade and the cutting surface by irradiating the tissue.

In an application, the optical fiber is positioned such that, during the surgical procedure, at least a distal portion of the optical fiber is in contact with the tissue that is disposed between the moving part and the other part of the mechanical cutting mechanism and is configured to deliver the laser energy directly to the tissue by emitting the laser energy from a lateral edge of the at least a distal portion of the optical fiber.

In an application, the optical fiber is configured to deliver the laser energy by emitting a beam of laser energy, and the tip includes a beam shaping element disposed at a distal end of the optical fiber, the beam shaping element configured to direct the beam of laser energy toward the tissue that is disposed between the moving part and the other part of the mechanical cutting mechanism.

In an application, the beam shaping element includes a line beam shaper configured to shape the emitted beam of laser energy into a line.

In an application, the optical fiber is configured to deliver the laser energy to the tip such that the laser energy leaves the tip and heats the tissue by irradiating the tissue through a fluid that surrounds the tissue.

In an application, the optical fiber is configured to deliver the laser energy to the tip such that the laser energy leaves the tip and heats the tissue to a temperature of at least 50 degrees Celsius.

In an application, the optical fiber is configured to deliver the laser energy to the tip such that the laser energy leaves the tip and heats the tissue to a temperature of at least 60-65 degrees Celsius.

In an application, the optical fiber is configured to deliver the laser energy to the tip such that the laser energy leaves the tip and heats the tissue so as to coagulate the irradiated tissue.

In an application, the apparatus includes an optical light guide disposed at least partially within the tip and coupled to a distal end of the optical fiber, the optical light guide configured to direct the laser energy toward the tissue that is disposed between the mechanical cutting blade and the cutting surface.

In an application, the optical light guide includes a coating configured to absorb at least some of the laser energy and thermally conduct the absorbed energy to the tissue by contacting the tissue that is disposed between the moving part of the mechanical cutting mechanism and the other part of the mechanical cutting mechanism.

In an application, the optical light guide is configured to direct the laser energy toward an energy-emitting surface of the light guide that is positioned adjacent to the cutting surface, such that laser energy emitted from the energy-emitting surface is directed toward the tissue that is disposed between the mechanical cutting blade and the cutting surface.

In an application, the energy-emitting surface includes a coating configured to absorb at least some of the laser energy and thermally conduct the absorbed energy to the tissue by contacting the tissue that is disposed between the moving part of the mechanical cutting blade and the cutting surface.

In an application, the optical light guide includes at least one internal reflective surface that is disposed at an angle so as to reflect the laser energy from the optical fiber toward the tissue that is disposed between the mechanical cutting blade and the cutting surface.

In an application, the at least one internal reflective surface is disposed at an angle of 10-41 degrees with respect to a central longitudinal axis of the optical fiber.

In an application, the optical light guide includes a high-melting-point material.

In an application, the optical light guide includes sapphire or diamond.

In an application, the distal portion of the elongate shaft includes a shape-changing region that is configured to change shape during the surgical procedure.

In an application, the shape-changing region has a bend radius that is less than 30 mm.

In an application, the shape-changing region is articulatable to an angle of up to 35 degrees, with respect to a central longitudinal axis of the optical fiber.

In an application, a widest part of the shape-changing region has a cross-section perpendicular to a longitudinal axis of the shape-changing region, the cross-section having a width of less than 3 mm.

In an application, the shape-changing region is configured to change shape under active control by the handle.

In an application, the shape-changing region is configured to change shape more in a first plane than in a second plane perpendicular to the first plane.

In an application, the apparatus includes an actuator that extends distally to the shape-changing region,
the shape-changing region includes a side-plate, the side-plate having a relaxed state and a deflected state, and
the actuator is operatively coupled to the side-plate such that actuation of the side-plate by the actuator causes the side-plate to flex along the first plane, such that the side-plate transitions from the relaxed state to the deflected state.

In an application, the side-plate has a greatest thickness of between 0.1-0.5 mm.

In an application, the side-plate has a greatest thickness less than 0.3 mm.

In an application:
the moving part of the mechanical cutting mechanism includes a first jaw,
the other part of the mechanical cutting mechanism includes a second jaw, and
the first and second jaws are coupled to each other at a jaw-hinge, such that the mechanical cutting mechanism is configured to cut the tissue disposed between the two jaws as the first jaw pivots about the jaw-hinge toward the second jaw.

In an application, the first and second jaws are curved such that the second jaw is placeable on a flat surface in a manner in which (a) the first jaw can articulate toward and away from the flat surface, and (b) the curve of the first and second jaws is in a plane that is parallel to the flat surface.

In an application, the curve of the first and second jaws has a radius of curvature of 3-20 mm.

In an application, the curve of the first and second jaws has an arc length of 6-20 mm.

In an application, the optical fiber is configured to deliver the laser energy to the tip such that the laser energy leaves the tip and irradiates the tissue that is disposed between the first jaw and the second jaw.

In an application, the optical fiber is configured to deliver the laser energy to the tip such that the laser energy leaves the tip and irradiates the tissue through a fluid that surrounds the tissue.

In an application, the optical fiber is configured to deliver the laser energy to the tip such that the laser energy leaves the tip and heats the tissue to a temperature of at least 50 degrees Celsius causing coagulation of the irradiated tissue.

In an application, the optical fiber is configured to deliver the laser energy to the tip such that the laser energy leaves the tip and heats the tissue to a temperature of 60-65 degrees Celsius causing coagulation of the irradiated tissue.

In an application, the apparatus includes an optical light guide disposed at least partially within the tip and coupled to a distal end of the optical fiber, the optical light guide configured to direct the laser energy toward the tissue that is disposed between the first jaw and the second jaw.

In an application, the optical light guide includes at least one internal reflective surface that is disposed at an angle so as to reflect the laser energy from the optical fiber toward the tissue that is disposed between the first jaw and the second jaw.

In an application, the optical light guide includes a coating configured to absorb at least some of the laser energy and thermally conduct the absorbed energy to the tissue by contacting the tissue that is disposed between the first jaw and the second jaw.

In an application, the optical light guide includes a high-melting-point material.

In an application, the optical light guide includes sapphire or diamond.

In an application, the optical light guide is disposed along the first jaw.

In an application:

the first and second jaws are curved such that the second jaw is placeable on a flat surface in a manner in which (a) the first jaw can articulate toward and away from the flat surface, and (b) the curve of the first and second jaws is in a plane that is parallel to the flat surface, and the optical light guide has the same curve as the first jaw.

In an application, the optical light guide is disposed along the second jaw.

In an application:

the first and second jaws are curved such that the second jaw is placeable on a flat surface in a manner in which (a) the first jaw can articulate toward and away from the flat surface, and (b) the curve of the first and second jaws is in a plane that is parallel to the flat surface, and the optical light guide has the same curve as the second jaw.

In an application, the optical fiber is positioned such that, during the surgical procedure, at least a distal portion of the optical fiber is in contact with the tissue that is disposed between the first jaw and the second jaw and is configured to deliver the laser energy directly to the tissue by emitting the laser energy from a lateral edge of the at least a distal portion of the optical fiber.

In an application, the at least a distal portion of the optical fiber is disposed along the first jaw.

In an application, the at least a distal portion of the optical fiber is disposed along the second jaw.

In an application:

the other part of the mechanical cutting mechanism includes a grasper (a) having first and second grasping elements, and (b) configured to grasp tissue of the subject between the first and second grasping elements, and the moving part of the mechanical cutting mechanism is a mechanical cutting blade disposed within the grasper and configured to slide with respect to the grasper to cut the grasped tissue.

In an application:

the first and second grasping elements include a first jaw and a second jaw, respectively, (a) the first and second jaws being coupled to each other at a jaw-hinge, and (b) the grasper being configured to grasp the tissue of the subject between the first and second jaws, and the mechanical cutting blade is disposed within the second jaw and is configured to slide longitudinally with respect to the second jaw to cut the tissue grasped between the first and second jaws.

In an application:

the first and second grasping elements include a first jaw and a second jaw, respectively, (a) the first and second jaws being coupled to each other at a jaw-hinge, and (b) the grasper being configured to grasp the tissue of the subject between the first and second jaws, and the mechanical cutting blade is disposed within the first jaw and is configured to slide longitudinally with respect to the first jaw to cut the tissue grasped between the first and second jaws.

In an application, the optical fiber is configured to deliver the laser energy to the tip such that the laser energy leaves the tip and heats the tissue that is disposed between the mechanical cutting blade and the grasper by irradiating the tissue.

In an application, the optical fiber is configured to deliver the laser energy to the tip such that the laser energy leaves the tip and heats the tissue by irradiating the tissue through a fluid that surrounds the tissue.

In an application, the optical fiber is configured to deliver the laser energy to the tip such that the laser energy leaves the tip and heats the tissue to a temperature of at least 50 degrees Celsius.

In an application, the optical fiber is configured to deliver the laser energy to the tip such that the laser energy leaves the tip and heats the tissue so as to coagulate the irradiated tissue.

In an application, the optical fiber is configured to deliver the laser energy to the tip such that the laser energy leaves the tip and heats the tissue to a temperature of 60-65 degrees Celsius.

In an application, the optical fiber is configured to deliver the laser energy to the tip such that the laser energy leaves the tip and heats the tissue so as to coagulate the irradiated tissue.

In an application, the mechanical cutting blade includes an optical light guide coupled to a distal end of the optical fiber, the optical light guide configured to direct the laser energy toward the tissue that is disposed between the mechanical cutting blade and the grasper.

In an application, the optical light guide includes at least one internal reflective surface that is disposed at an angle so as to reflect the laser energy from the optical fiber toward the tissue.

In an application, the at least one internal reflective surface is disposed at an angle of 10-41 degrees with respect to a central longitudinal axis of the optical fiber.

In an application, the optical light guide includes a coating configured to absorb at least some of the laser energy and thermally conduct the absorbed energy to the tissue by contacting the tissue that is disposed between the mechanical cutting blade and the grasper.

In an application, the optical light guide includes a high-melting-point material.

In an application, the optical light guide includes sapphire or diamond.

The present invention will be more fully understood from the following detailed description of applications thereof, taken together with the drawings, in which:

BRIEF DESCRIPTION OF THE DRAWINGS

FIGS. 5A-I are schematic illustrations of a configuration of the tip of the surgical tool, in accordance with some applications of the present invention;

FIGS. 6A-H are additional schematic illustrations of a configuration of the tip of the surgical tool, in accordance with some applications of the present invention;

FIGS. 7A-D are schematic illustrations of a biter configuration for the tip of the surgical tool, in accordance with some applications of the present invention;

FIGS. 12A-C and 13A-D are schematic illustrations showing use of the configuration of the tip shown in FIGS. 9A-C, in accordance with some applications of the present invention;

FIGS. 14A-D are schematic illustrations of a configuration for the shape-changing region of the shaft, in accordance with some applications of the present invention.

DETAILED DESCRIPTION

Figure 1A:
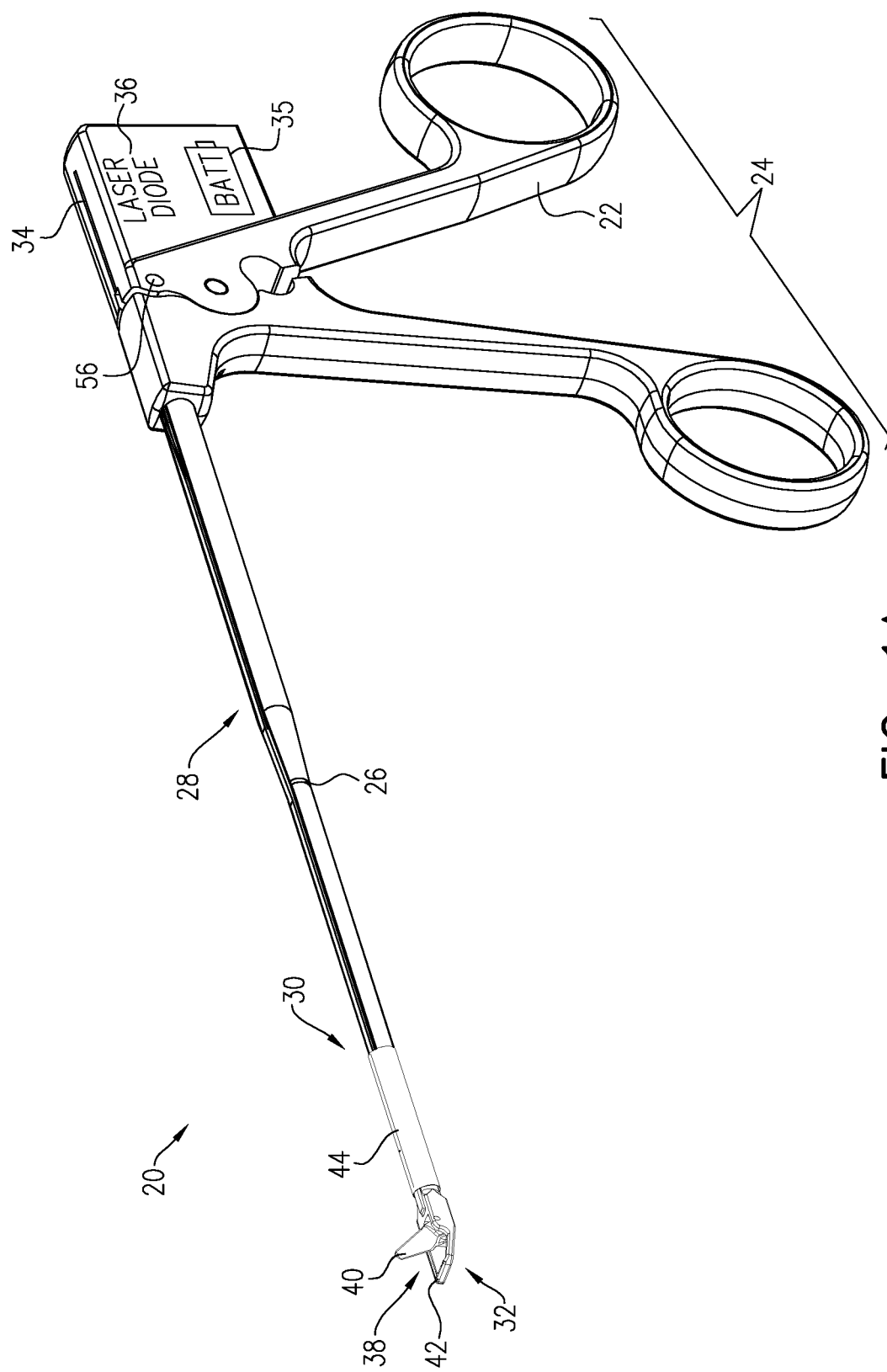
FIGS. 1A-B are schematic illustrations of a surgical tool in accordance with some applications of the present invention.
Figure 1B:
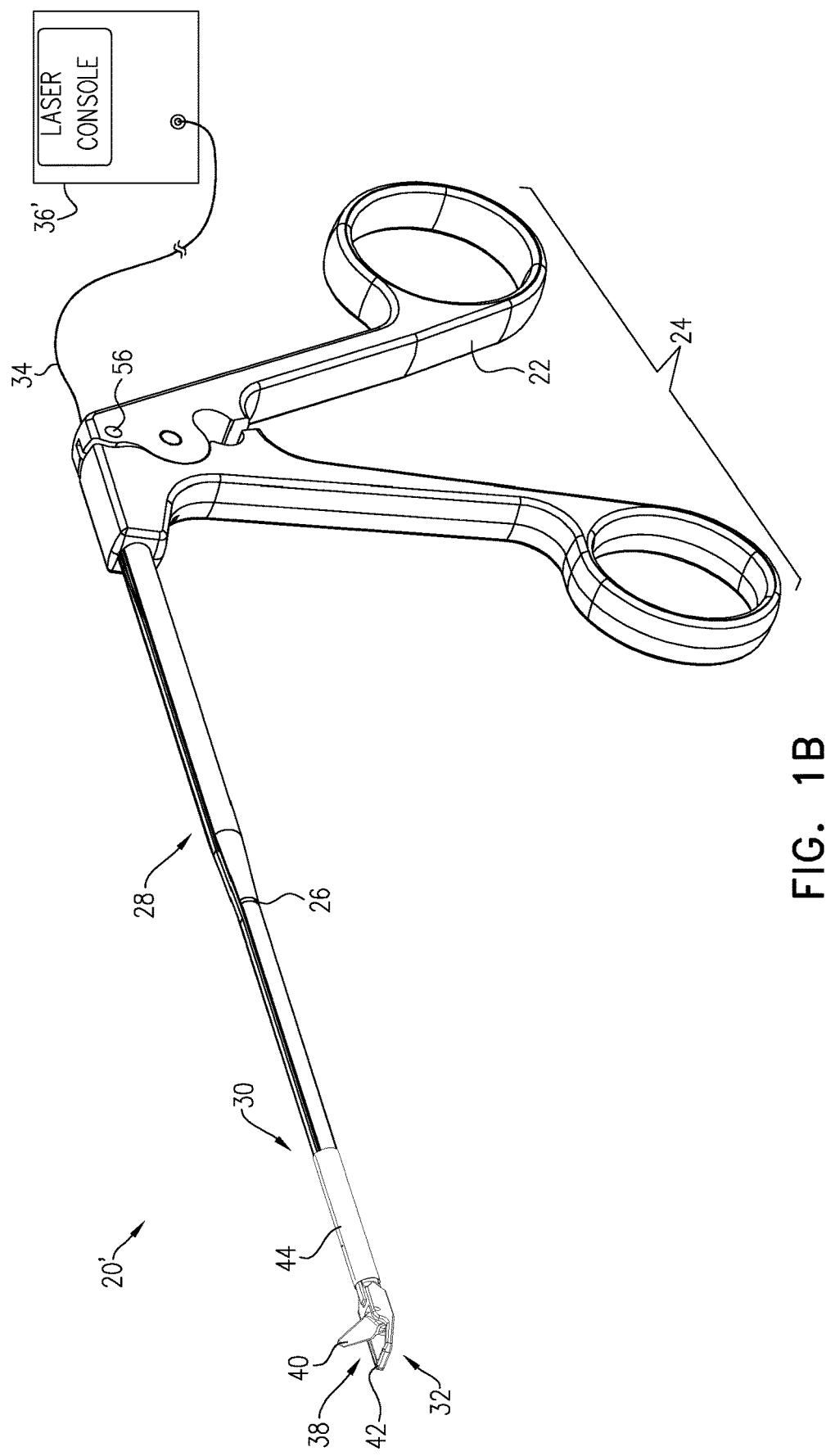

Reference is now made to FIGS. 1A-B, which are schematic illustration of a surgical tool 20, 20' in accordance with some applications of the present invention. A handle 22 is disposed at a proximal end 24 of tool 20, 20'. An elongate shaft 26 extends from handle 22 in a distal direction. Shaft 26 has a proximal portion 28 and a distal portion 30. Distal portion 30 of elongate shaft 26 is sized and shaped to be inserted into a subject during a surgical procedure and to contact tissue of the subject. A tip 32 is disposed at distal portion 30 of elongate shaft 26. It is noted that the specific tip illustrated in FIGS. 1A-B is a non-limiting example, and various different applications for tip 32 are described hereinbelow.

An optical fiber 34 delivers laser energy to tip 32. Optical fiber 34 is typically coupled to a laser 36, 36', e.g., a laser diode, laser diode array, or diode pump solid state laser. For some applications, laser 36 may emit laser energy at a wavelength of at least 300 nanometers and/or less than 3 micrometers, e.g., at a wavelength of at least 750 nanometers and/or less than 1500 nanometers, e.g., 980 nanometers or 1470 nanometers. For some applications, and as shown in FIG. 1A, power is supplied to laser 36 from within tool 20 (e.g., from a battery 35). Alternatively or in addition, and as shown in FIG. 1B, laser 36' may include a console that is connected to tip 32 via optical fiber 34. Typically for such applications, power is supplied to laser 36' from a source external to tool 20'.

Tip 32 has a mechanical cutting mechanism 38 that has a moving part 40 that moves with respect to another part 42 in order to cut tissue of the subject that is disposed between parts 40 and 42. It is noted that the specific moving part 40 and other part 42 illustrated in FIGS. 1A-B is a non-limiting example, and various different configurations for moving part 40 and other part 42 are described hereinbelow. As described hereinabove, the laser energy enables mechanical cutting mechanism 38 to cut the tissue of the subject using a mechanical force that is lower than a mechanical force that would be required to cut the tissue in the absence of the laser energy. The laser energy in combination with the mechanical cutting also enables a faster cutting rate of the tissue than if the tissue were to be mechanically cut in the absence of the laser energy or if tissue were to be laser cut in the absence of mechanical force. For example, in an experiment carried out by the inventors, the cutting rate of the tissue when using the combination of laser energy and mechanical cutting was more than 10 times faster than the cutting rate of the tissue with laser energy alone, cutting an area of 6 mm^2 in less than 2 seconds with the combination of laser energy and mechanical cutting, versus more than 20 seconds with laser energy alone.

For some applications, distal portion 30 of shaft 26 has a shape-changing region 44 that is configured to change shape during the surgical procedure, such that tip 32 can articulate with respect to shaft 26. For some applications, shape-changing region 44 is configured to change shape under active control by handle 22. For example, there may be an articulation actuator (not shown), e.g., knob or slide-bar, disposed on handle 22 that is actively connected to an articulation mechanism in order to control shape-changing region 44, as is known in the art of minimally invasive devices.

Figure 1C:
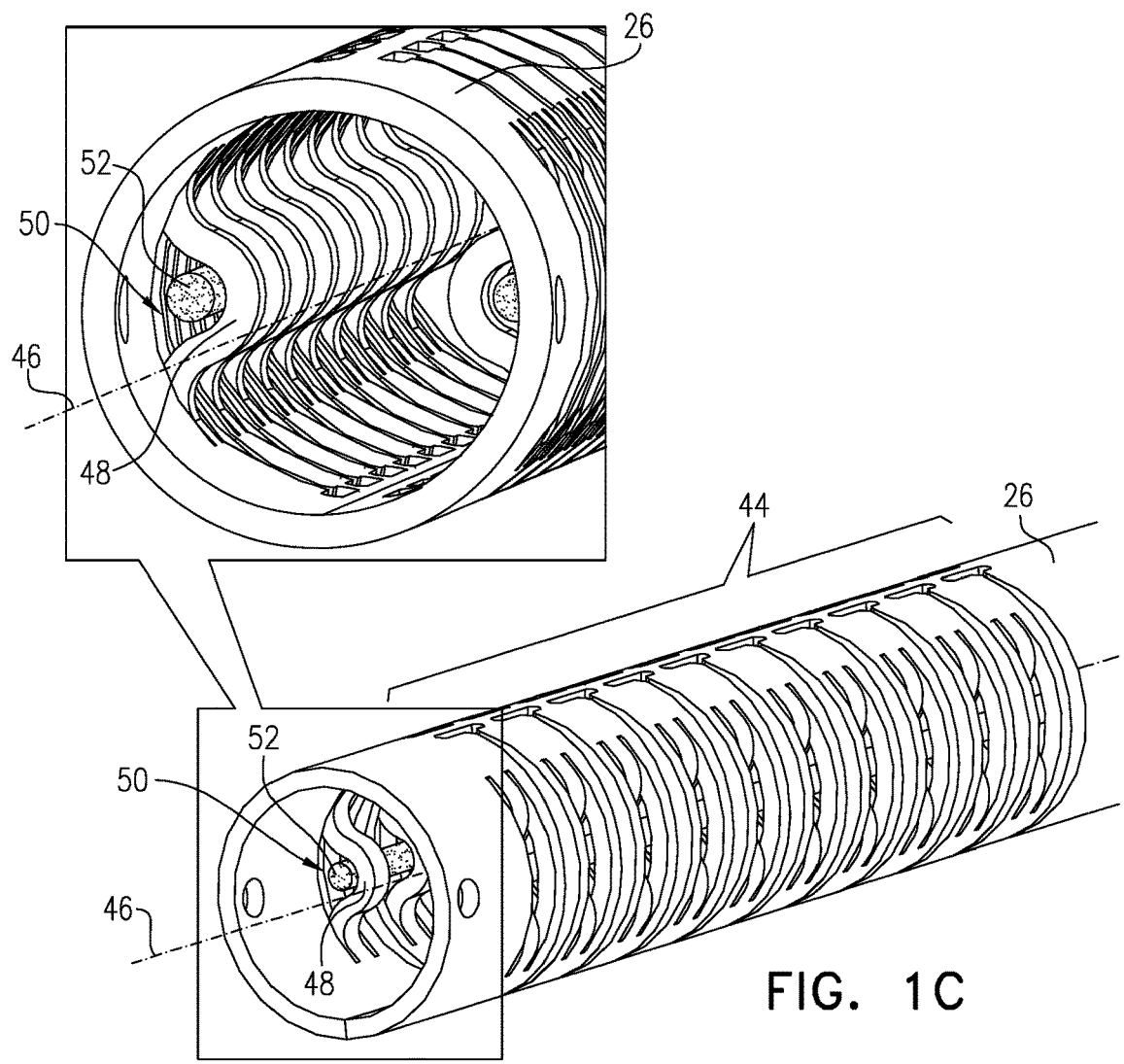
FIGS. 1C-D are schematic illustrations of a shape-changing region of a shaft of the surgical tool, in accordance with some applications of the present invention.

Reference is now made to FIG. 1C, which is a schematic illustration of a configuration for shape-changing region 44, in accordance with some applications of the present invention. For some applications, shape-changing region 44 may be implemented as a stainless-steel hollow pipe (or a pipe made of another material) that is laser-cut to allow the stainless-steel pipe to be flexible, as shown in FIG. 1C. The design of the laser cut typically enables the pipe to flex more in a first plane than in a second plane that is perpendicular to the first plane. The first plane is typically coplanar with a central longitudinal axis 46 of shaft 26, such that the pipe flexes laterally, thereby allowing tip 32 to articulate laterally. For some applications, the laser cut design creates a series of pipe segments 48 that can be pushed inwardly toward central longitudinal axis 46 in order to create two side-channels 50 on opposite sides of shape-changing region 44 (for example, the channels may be coplanar with central longitudinal axis 46 as shown). A metal wire 52, e.g., a nitinol wire, may be threaded through each channel 50 and welded at a distal end to shaft 26 (welding not shown). A proximal end of each metal wire 52 is coupled to the articulation actuator, e.g., knob or slide bar. As the articulation actuator pulls metal wires 52 independently of each other based on direction of actuation, shape-changing region 44 (i.e., the laser cut pipe) articulates from side-to-side, so as to allow a surgeon to control the angle of tip 32 with respect to shaft 26. For some applications, alternatively or additionally to a laser-cut hollow pipe, shape-changing region 44 may be implemented as concatenated pipe segments.

Figure 1D:
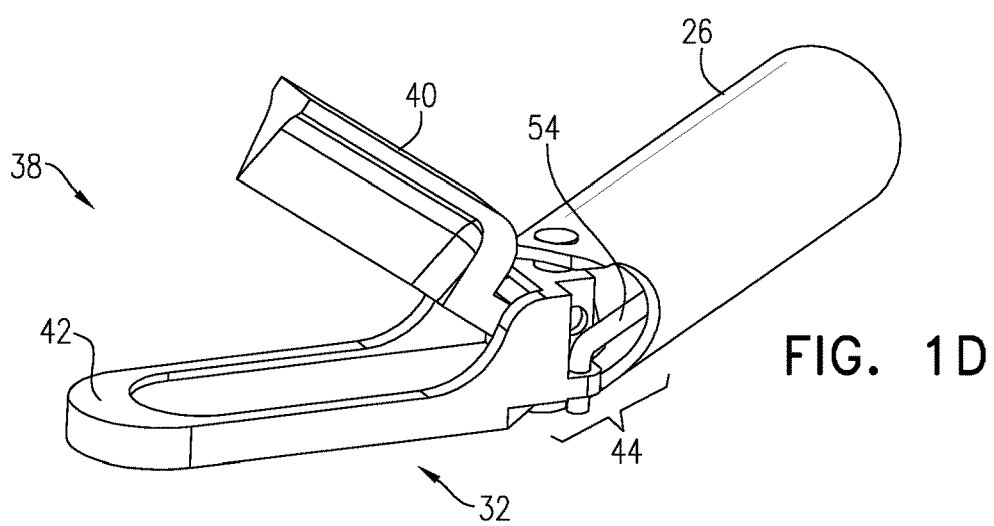

Reference is now made to FIG. 1D, which is a schematic illustration of a configuration for shape-changing region 44, in accordance with some applications of the present invention. For some applications, two rigid rods 54 (for illustrative purposes only one rod 54 is shown in FIG. 1D) may be disposed within shaft 26, each coupled at a distal end to a lateral side of tip 32 (e.g., to part 42 thereof). Proximal ends of rigid rods 54 are coupled to the articulation actuator. In this configuration, the articulation actuator is configured to push on one rod 54 as it pulls on the other rod 54, and vice versa, in order to cause tip 32 (and therefore cutting mechanism 38, in the embodiment shown in FIG. 1D) to articulate laterally with respect to shaft 26, so as to allow a surgeon to control the angle of tip 32 with respect to shaft 26.

For some applications, shape-changing region 44 is implemented as a deformable (e.g., plastically deformable) distal portion of shaft 26 that a surgeon can bend before or during a procedure to whatever orientation is desired. For some applications, the deformation is easily reversible, e.g., if the surgeon chooses to form shape-changing region 44 into a different shape.

Figure 1E:
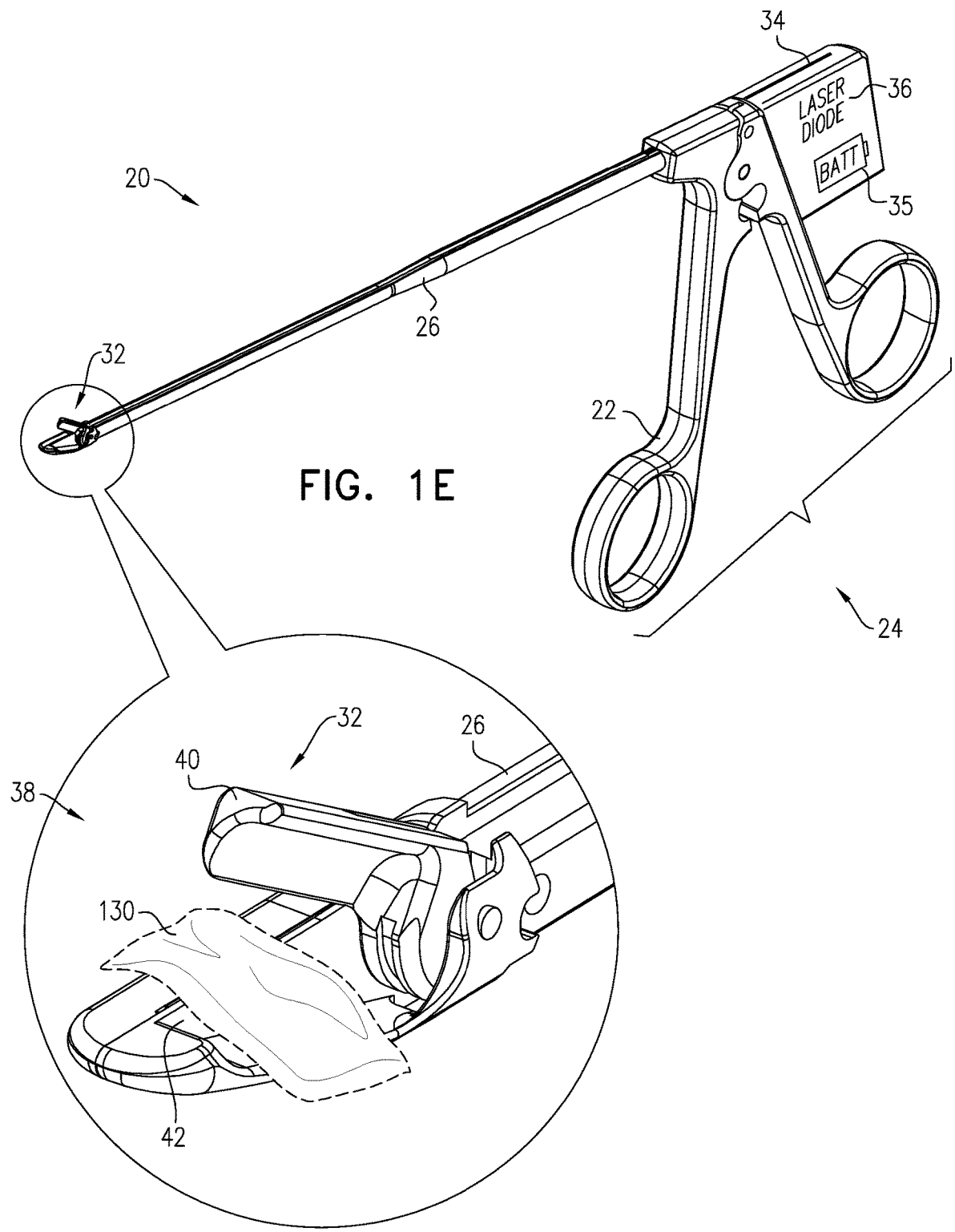
FIG. 1E is a schematic illustration showing an example of use of a surgical tool, in accordance with some applications of the present invention.

Reference is now made to FIG. 1E, which shows tip 32 and a portion of tissue 130 of the subject disposed between moving part 40 and other part 42 of mechanical cutting mechanism 38. The following is a non-limiting list of examples of tissue 130 of the subject and different types of surgeries in which tool 20 may be used:
  a meniscus of a knee of the subject, e.g., in a meniscectomy,
  tissue of the hip, e.g., in a hamstring repair, or gluteus medius repair,
  tissue of the shoulder, e.g., in a shoulder synovectomy, frozen shoulder surgery, arthroscopic capsular release, rotator cuff repair,
  a tendon or ligament, e.g., for use in arthrolysis,
  tissue of the bicep, e.g., in a biceps tenotomy,
  hemorrhoid removal,
  tissue of the hand, e.g., in carpel tunnel surgery,
  removal of fecal impaction,
  adenoidectomy,
  hysteroscopic surgery, e.g., removal of pedunculated submucosal fibroids
  laparoscopic surgery, e.g., removal of subserosal fibroids
  abdominal surgery, e.g., performed laparoscopically,
  cyst cutting, and
  endoscopic stomach polyp removal.
It is noted that although the particular mechanical cutting mechanism 38 shown in FIG. 1E utilizes a mechanical cutting blade 40 that slides against a cutting surface 42, this is non-limiting and just for illustrative purposes. Any of the configurations for mechanical cutting mechanism 38 described herein may be used, mutatis mutandis, in any of the abovementioned types of surgeries.

Figure 2:
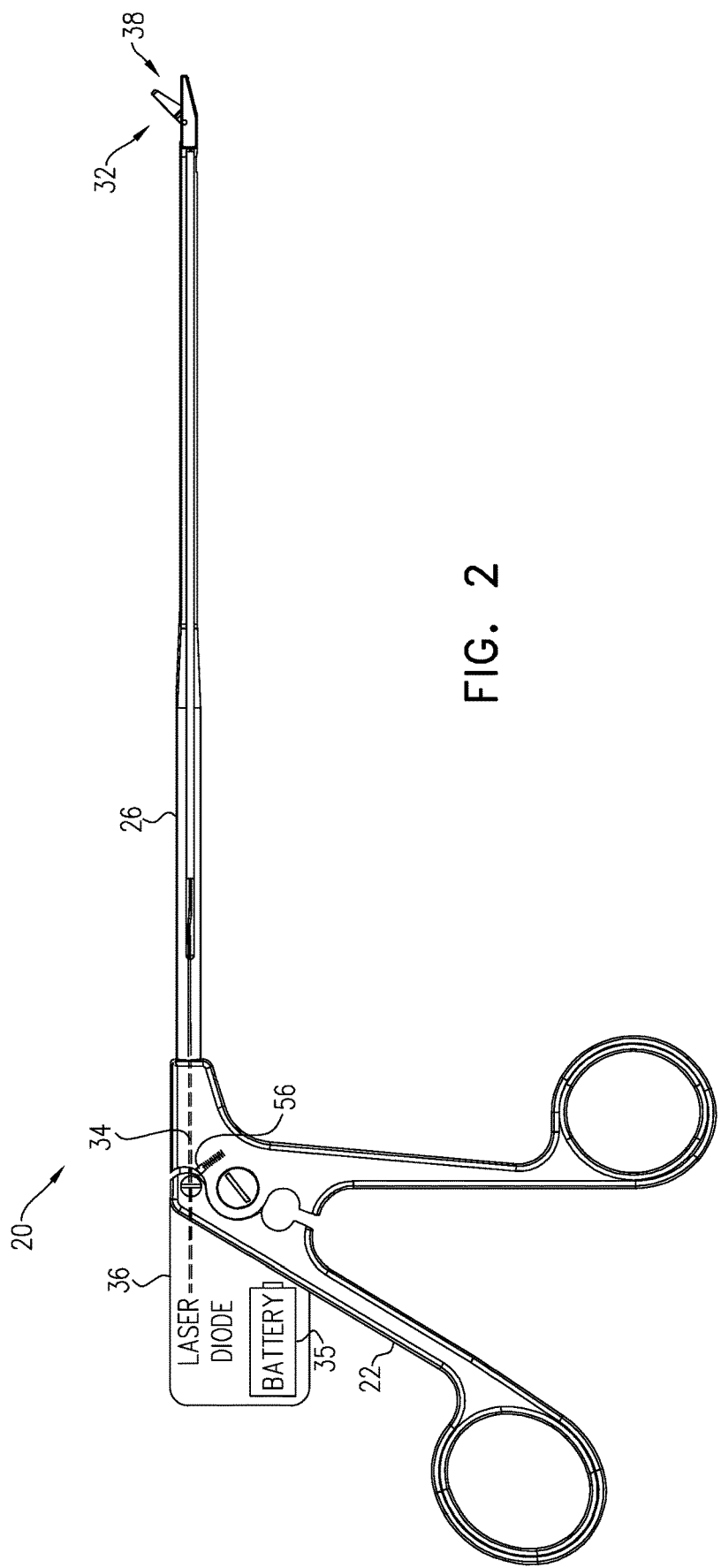
FIG. 2 is a schematic illustration of a side-view of the surgical tool, in accordance with some applications of the present invention.

Reference is now made to FIG. 2, which is a schematic illustration of a side-view of tool 20, in accordance with some applications of the present invention. For some applications, a microswitch 56 is located on handle 22 and configured to automatically operate laser 36 generally simultaneously with the actuation of mechanical cutting mechanism 38, such that optical fiber 34 delivers the laser energy to tip 32 upon activation of microswitch 56. Alternatively, a foot-switch or activation button or trigger (not shown) is provided for manual activation of laser 36, such that optical fiber 34 delivers the laser energy to tip 32 upon activation of the foot switch or activation button. For some applications, laser 36 may be activated prior to the actuation of mechanical cutting mechanism 38, simultaneously with the actuation of mechanical cutting mechanism 38, or following the actuation of mechanical cutting mechanism 38. This allows the surgeon to position tip 32 at a desired location and to position the desired tissue to be cut between moving part 40 and other part 42 of mechanical cutting mechanism 38 prior to activating laser 36.

Typically for applications in which laser 36 is activated at the same time as mechanical cutting mechanism 38 is actuated using handle 22, the tissue cutting begins at the same time the laser energy is delivered to tip 32. Typically for such applications, the photothermal effect of the laser energy that (a) softens (by heating) the tissue, (b) reduces the force required for the mechanical cutting and, (c) at the same time coagulates the cut tissue, occurs substantially immediately upon activation of laser 36. It is noted again that the specific configuration for tip 32 shown in FIG. 2 is a non-limiting example for illustrative purposes and that tip 32 can be implemented with various different configurations as further described hereinbelow.

For some applications, optical fiber 34 is configured to deliver the laser energy to tip 32 such that the laser energy leaves tip 32 and heats the tissue that is disposed between moving part 40 and other part 42 of mechanical cutting mechanism 38 by irradiating the tissue. Since this type of surgery is often performed in a setting that is being flushed or inflated with fluid, e.g., flushed with a liquid such as saline, or inflated with a gas (for example, in the case of laparoscopic surgeries), for some applications the laser energy heats the tissue by irradiating the tissue through a fluid that surrounds the tissue. Typically, the tissue is heated by the laser energy to a temperature of at least 50 degrees Celsius, e.g., at least 60 degrees Celsius and/or less than 65 degrees Celsius (alternatively or additionally between 60+/−5 degrees Celsius and 65+/− degrees Celsius), which, as described hereinabove, is low enough to avoid typically undesired effects on the tissue (e.g., denaturization, dehydration, and/or carbonization), but high enough to allow the mechanical cutting of the tissue to use less force and to coagulate the cut tissue. For some applications, a temperature sensor is disposed on or near tip 32 and connected to a processor and feedback monitor so as to measure and display the temperature of the tissue, enabling the surgeon to monitor that the tissue is being heated to the desired temperature.

Figure 3A:
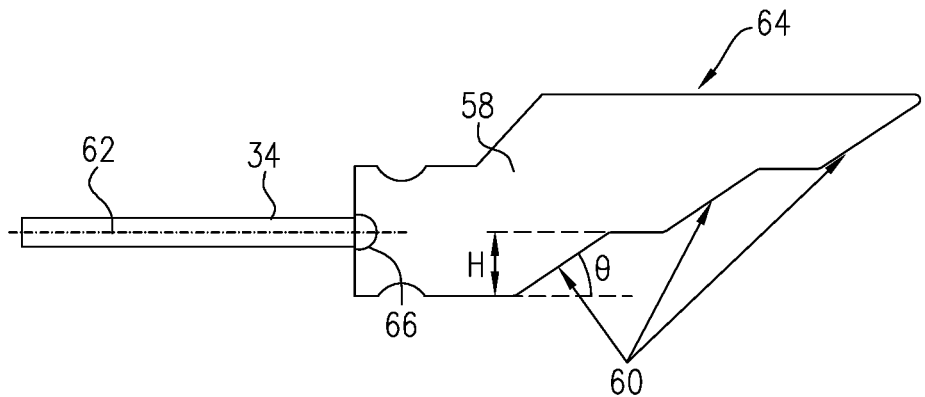
FIGS. 3A-B are schematic illustrations of an optical light guide, in accordance with some applications of the present invention.
Figure 3B:
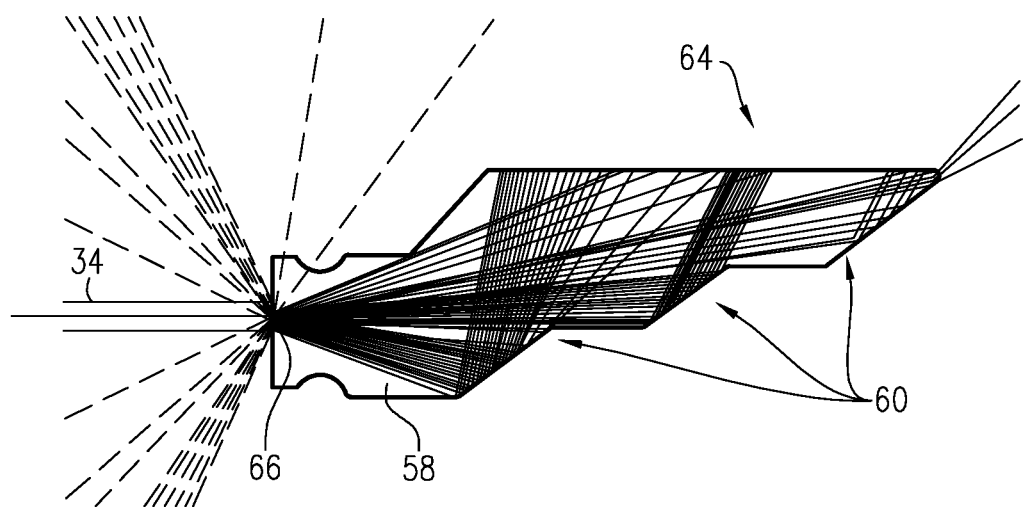

Reference is now made to FIGS. 3A-B, which are schematic illustrations of an optical light guide 58 that is coupled to a distal end of optical fiber 34, in accordance with some applications of the present invention. Optical light guide 58 is typically disposed at least partially within tip 32 (as further described hereinbelow) and is configured to direct the laser energy toward the tissue that is disposed between moving part 40 and other part 42 of mechanical cutting mechanism 38. Optical light guide 58 is typically made from a high-melting point material, such as sapphire or diamond. Optical light guide 58 has at least one internal reflective surface 60 that is disposed at an angle so as to reflect the laser energy from the optical fiber toward the tissue, e.g., utilizing total internal reflection (TIR). Typically, in order to achieve TIR within optical light guide 58, reflective surface 60 is disposed at an angle theta of at least 10 degrees and/or less than 41 degrees with respect to a central longitudinal axis 62 of optical fiber 34. A height H of reflective surface(s) 60 is determined empirically by energy optimization along an upper energy-emitting surface 64. An input lens 66 or other optical element is used to spread out the laser light as it enters optical light guide 58 in order to fill energy-emitting surface 64 with light. FIG. 3B shows a ray-tracing diagram in which high-intensity light is shown as solid lines, and low-intensity scattered light is shown as dashed lines. As shown, the laser energy is delivered by optical fiber 34 to optical light guide 58, into which input lens 66 spreads out the laser light, and reflective surface(s) 60 reflect the laser light within optical light guide 58 toward upper energy-emitting surface 64.

For some applications, optical light guide 58 is not used and optical fiber 34 is positioned such that, during the surgical procedure, at least a distal portion of optical fiber 34 is in contact with or is adjacent to the tissue that is disposed between moving part 40 and other part 42 of mechanical cutting mechanism 38, and is configured to deliver the laser energy directly to the tissue by emitting the laser energy, e.g., from a lateral edge of the distal portion of optical fiber 34.

For some applications, optical fiber 34 is configured to deliver the laser energy to tip 32 by emitting a beam of laser energy, and tip 32 includes a beam shaping element, e.g., a line beam shaper, e.g., a Powell lens, or a Fresnel lens, disposed at a distal end of optical fiber 34. The beam shaping element is configured to direct the beam of laser energy toward the tissue that is disposed between moving part 40 and other part 42 of mechanical cutting mechanism 38.

Figure 4A:
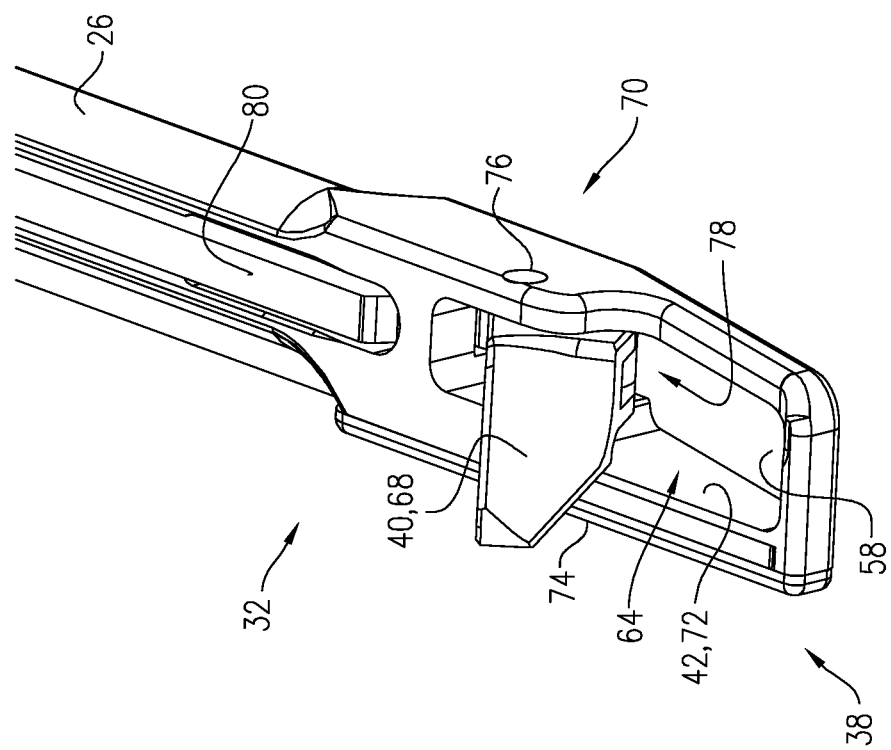
FIGS. 4A-C are schematic illustrations of a configuration of the tip of the surgical tool, in accordance with some applications of the present invention.
Figure 4B:
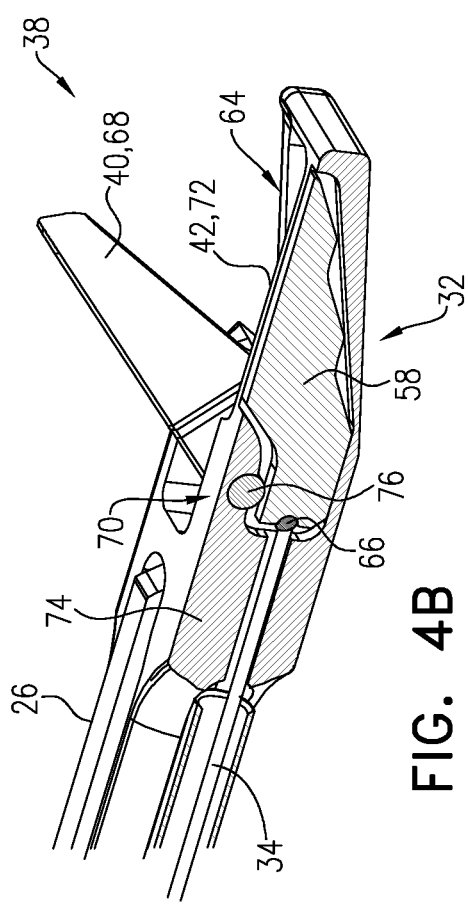
Figure 4C:
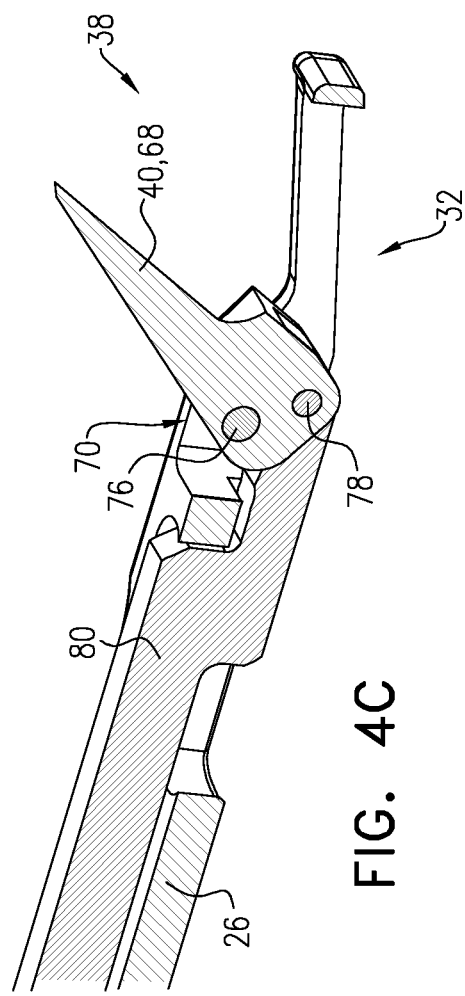

Reference is now made to FIGS. 4A-C, which are schematic illustrations of tip 32, in accordance with some applications of the present invention. For some applications and as shown, tip 32 is a cutting tip configured to cut tissue of the subject using a scissor-like cutting action. In this configuration, moving part 40 of mechanical cutting mechanism 38 is a mechanical cutting blade 68 that is coupled to tip 32 at a mechanical joint 70. Other part 42 of mechanical cutting mechanism 38 is a cutting surface 72 against which mechanical cutting blade 68 slides as mechanical cutting blade 68 pivots from an open position to a closed position.

Optical light guide 58 (shown in the cross-sectional view of tip 32 in FIG. 4B) is disposed at least partially within tip 32 and coupled to a distal end of optical fiber 34 (e.g., at input lens 66). Upon activation of laser 36, optical light guide 58 directs the laser energy toward the tissue that is disposed between mechanical cutting blade 68 and cutting surface 72. For some applications, energy-emitting surface 64 of optical light guide 58 is positioned adjacent cutting surface 72 (as shown in FIG. 4A). For some applications, surrounding optical light guide 58 has a light guide cover 74 which is used to mount optical light guide 58 within tip 32 and prevent tissue from coming into contact with the lateral sides of optical light guide 58.

Optical light guide 58 directs the laser energy toward energy-emitting surface 64, such that laser energy emitted from the energy-emitting surface is directed toward the tissue that is disposed between mechanical cutting blade 68 and cutting surface 72. In this manner, upon activation of laser 36, the laser energy leaves tip 32 and heats the tissue that is disposed between mechanical cutting blade 68 and cutting surface 72 by irradiating the tissue, e.g., by irradiating the tissue through a fluid that surrounds the tissue. As described hereinabove, the laser energy typically heats the tissue to a temperature of at least 50 degrees Celsius, e.g., at least 60 degrees Celsius and/or less than 65 degrees Celsius (alternatively or additionally between 60+/−5 degrees Celsius and 65+/− degrees Celsius), enabling mechanical cutting blade 68 to cut the tissue with lower mechanical force, at a faster cutting rate, and while coagulating the tissue as it is cut.

FIG. 4C depicts an alternate cross-sectional view of tip 32, showing the mechanical actuation system for mechanical cutting blade 68. Mechanical joint 70 includes the pivot 76 around which mechanical cutting blade 68 pivots. A second pivot 78 is coupled to a mechanical actuator 80 that moves longitudinally back and forth with respect to shaft 26 upon activation by handle 22 in order to cause mechanical cutting blade 68 to pivot.

The following are descriptions of two experiments carried out by the inventors for the above-described implementation of tool 20:

Experiment 1

The test was conducted using the following setup:
Laser type: diode array
Wavelength: 1470 nm
Laser power range: 7-45 W
Laser modulation: ranging from 100 microsecond-long pulses to continuous wave (CW) at 10-100% duty cycle
Beam Delivery: fiber optic 360 micrometer core 0.22 NA
Laser power test equipment: thermopile power meter (to test laser power)
Laser modulation test equipment: digital oscilloscope
Tested substrate: animal (pig) meniscus Laboratory Test Results of Experiment 1

1. Cutting of animal meniscus with the experimental setup using a diamond blade without laser energy was not possible (the force needed was greater than 2 N, beyond the force enabled by the experimental setup)
2. Cutting of animal meniscus with the experimental setup using a diamond blade with laser energy resulted in smooth cutting and coagulation of the treated area at a force below 0.5 N, within the following average power ranges in dry conditions: 12 W CW, 15 W CW, 20 W CW, 25 W CW, and 30 W CW, and within the following average power ranges in saline-immersed conditions: 18 W CW, 25 W, and 30 W CW. At 40 W of power, carbonization effects in the tissue started to be seen.

Experiment 2

The test was conducted using the following setup:
Laser type: diode array
Wavelength: 1470 nm
Laser power range: 7-45 W
Laser modulation: ranging from 100 microsecond-long pulses to continuous wave (CW) at 10-100% duty cycle
Beam Delivery: fiber optic 360 micrometer core 0.22 NA
Laser power Test Equipment: thermopile power meter (to test laser power)
Laser modulation test equipment: fast photodiode, digital oscilloscope
Tested substrate: animal (pig) meniscus Laboratory Test Results of Experiment 2

1. Cutting of animal meniscus with the experimental setup using a diamond blade without laser energy was not possible (the force needed was beyond the force enabled by the experimental setup).

2. Cutting of animal meniscus with the experimental setup using a diamond blade with laser energy resulted in smooth cutting and coagulation of the treated area within the following average power ranges: 15-30 W in CW mode.

It is noted that while a laser of a specific wavelength was used in the experimental setup, as described hereinabove with reference to FIG. 1, laser 36 may emit laser energy for example at a wavelength of at least 300 nanometers and/or less than 3 micrometers, e.g., at a wavelength of at least 750 nanometers and/or less than 1500 nanometers, e.g., 980 nanometers or 1470 nanometers.

Figure 5C:
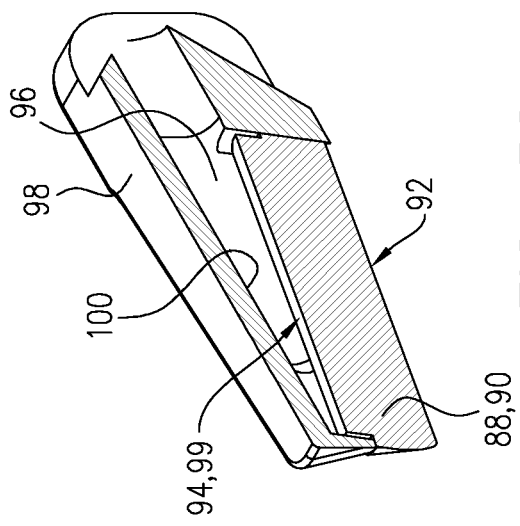
Figure 5E:
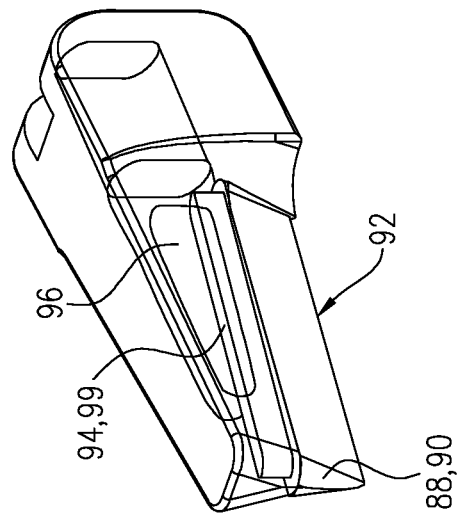

Reference is now made to FIGS. 5A-I, which are schematic illustration of tip 32, in accordance with some applications of the present invention. FIG. 5A depicts another configuration for mechanical cutting mechanism 38. For some applications, moving part 40 of mechanical cutting mechanism 38 comprises a mechanical cutting blade 82 that is coupled to tip 32 at a mechanical joint 84. Other part 42 of mechanical cutting mechanism 38 is a tissue-stabilizing base 86 configured to stabilize the tissue disposed between mechanical cutting blade 82 and tissue-stabilizing base 86 as mechanical cutting blade 82 cuts the tissue by pivoting toward tissue-stabilizing base 86.

Similarly to mechanical joint 70 described hereinabove with reference to FIGS. 4A-C, a mechanical joint 84 includes pivot 76 around which mechanical cutting blade 82 pivots. Second pivot 78 is coupled to mechanical actuator 80 that moves longitudinally back and forth with respect to shaft 26 upon activation by handle 22, in order to cause mechanical cutting blade 82 to pivot.

In contrast to the direct laser irradiation of the tissue described hereinabove, where the laser energy leaves tip 32, for some applications, at least a portion 88 of moving part 40, e.g., mechanical cutting blade 82, of mechanical cutting mechanism 38 is either (a) made from, or (b) coated in, a highly absorptive material that has low thermal mass and high thermal conductivity, such that it absorbs the laser energy and thermally conducts the absorbed laser energy to the tissue by contacting the tissue that is disposed between moving part 40, e.g., mechanical cutting blade 82, of mechanical cutting mechanism 38 and other part 42, e.g., tissue-stabilizing base 86, of mechanical cutting mechanism 38. In this case, the tissue is heated by direct contact with portion 88 of moving part 40, e.g., mechanical cutting blade 82.

For some applications, portion 88 of moving part 40, e.g., mechanical cutting blade 82 coagulates the tissue upon thermally conducting the absorbed laser energy to the tissue. Alternatively, for some applications, portion 88 of moving part 40, e.g., mechanical cutting blade 82, vaporizes the tissue upon thermally conducting the absorbed laser energy to the tissue. Using the laser energy to heat the tissue by direct contact with a part of tip 32 that has absorbed the laser energy and converted it to heat, as opposed to by irradiation, reduces the heat-affected zone of the tissue, since only the tissue that is in direct contact with portion 88 is heated. For example, direct contact of lower edge 92 with tissue may vaporize that tissue, and carbonize a thin (e.g., between 10 and 30 micrometer) layer of remaining tissue. Typically for such applications, tissue underlying the carbonized layer is coagulated, reducing the heat-affected zone of tissue, relative to when the tissue is heated by direct laser irradiation.

Figure 5B:
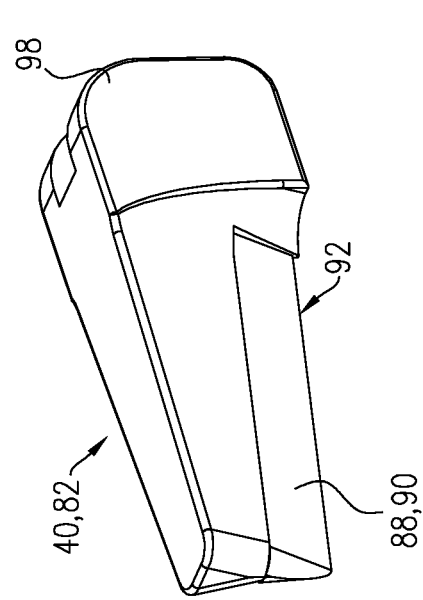

For some applications, the absorbed laser energy is thermally conducted to the tissue by portion 88 of moving part 40, e.g., mechanical cutting blade 82, of mechanical cutting mechanism 38 that is a tissue-cutting element 90 (shown in FIG. 5B). Tissue cutting element 90 is made from a highly absorptive material that has low thermal mass and high thermal conductivity. A lower edge 92 (shown in FIG. 5B and in FIG. 5C, which is a cross-sectional view of FIG. 5B) of tissue cutting element 90 faces the tissue that is disposed between moving part 40 and other part 42 of mechanical cutting mechanism 38, e.g., between mechanical cutting blade 82 and tissue-stabilizing base 86. An upper edge 94, opposite lower edge 92, faces away from the tissue.

For some applications, mechanical cutting blade 82 of mechanical cutting mechanism 38 is shaped to define a hollow cavity 96. As shown in the cross-sectional view of FIGS. 5C, 5G and 5I, upper edge 94 of tissue-cutting element 90 forms at least a portion of a lower surface 99 of hollow cavity 96.

Figure 5D:
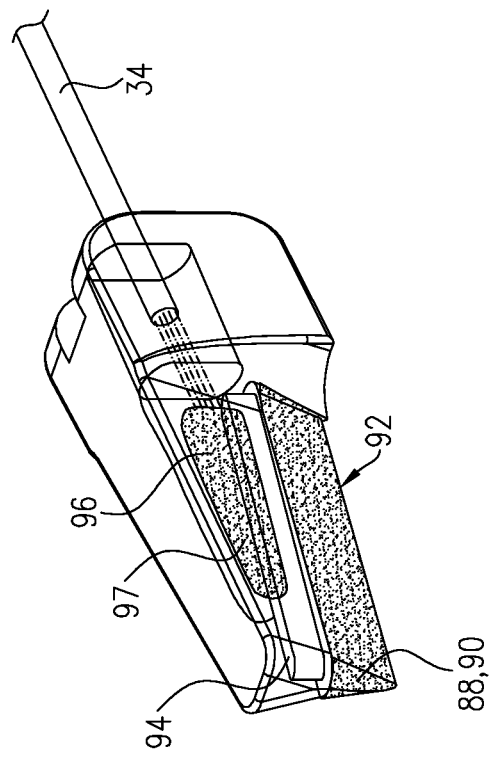
Figure 5F:
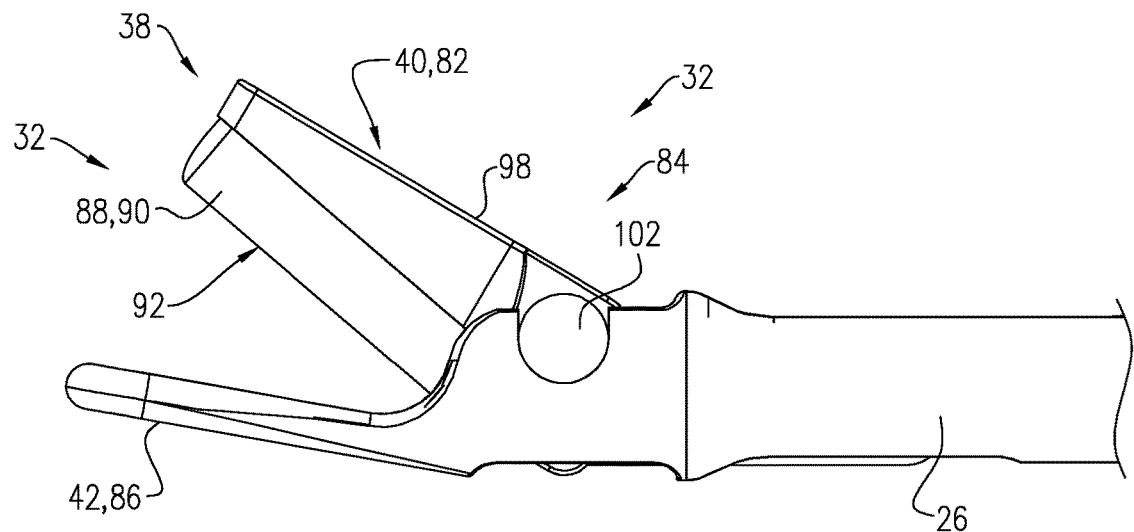
Figure 5G:
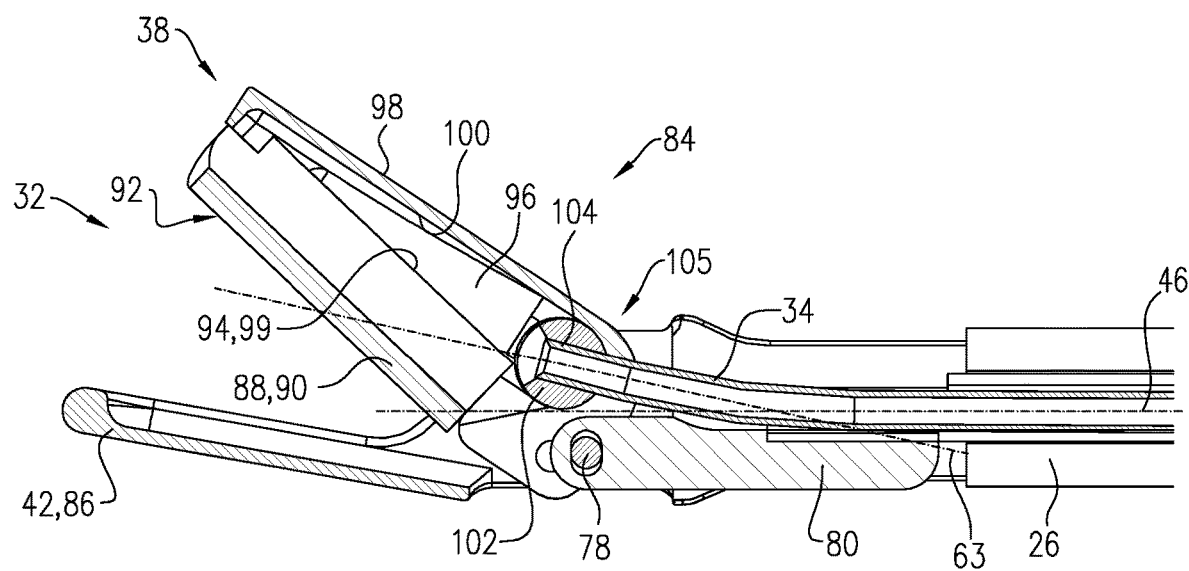
Figure 5H:
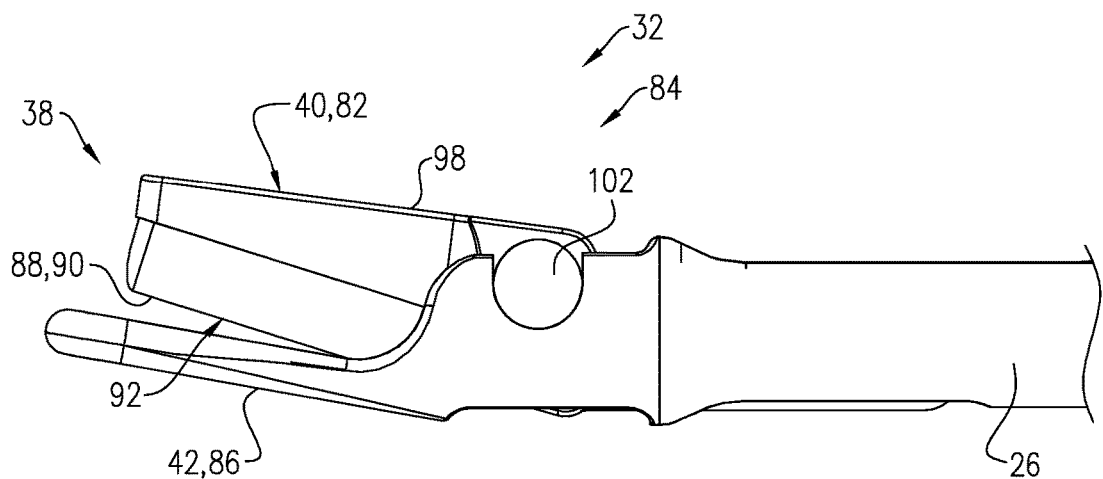
Figure 5I:
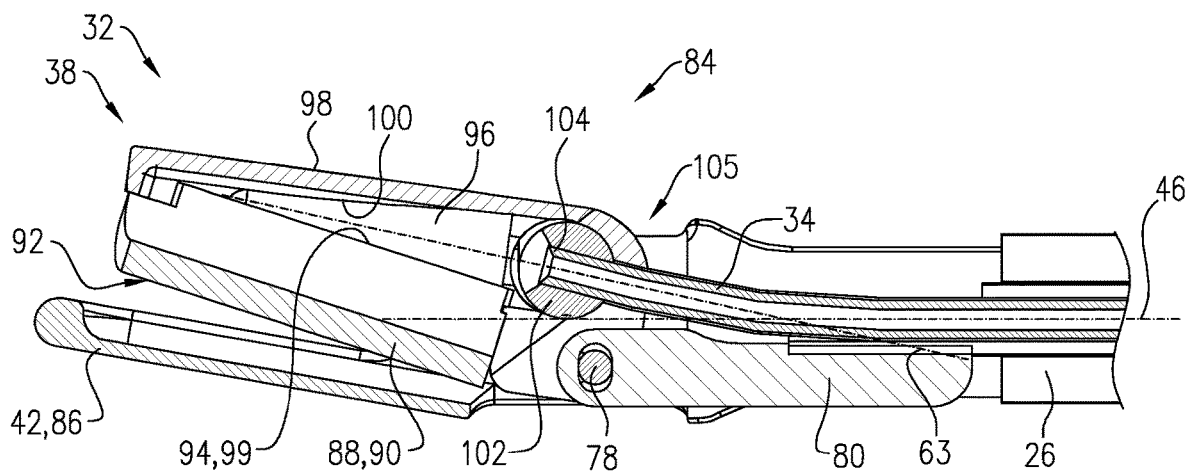

Upon activation of laser 36, optical fiber 34 delivers the laser energy into hollow cavity 96 (FIG. 5D). In contrast to the configuration described hereinabove with reference to FIGS. 3A-B and 4A-C, optical fiber 34 typically delivers the laser energy into hollow cavity 96 without a lens or other optical element that would spread out the laser light.

Typically, a body portion 98 of mechanical cutting blade 82 surrounding hollow cavity 96 is made from a material that has low thermal conductivity, such that as the laser energy is delivered into hollow cavity 96, the outside (e.g., the lateral sides and top) of mechanical cutting blade 82 are not heated significantly from the laser energy. For example, body portion 98 may be made of TCT97, Zirconia, or another ceramic compound.

Further typically, hollow cavity 96 has an internal upper surface 100 with high reflectivity. For some applications, internal upper surface 100 reflects at least 85 percent (e.g., at least 90 percent) of the laser energy that reaches the internal upper surface.

For some applications, the material that body portion 98 is made of has high reflectivity itself, resulting in internal upper surface 100 of hollow cavity 96 having high reflectivity. Alternatively or additionally, for some applications, internal upper surface 100 of hollow cavity 96 is a reflective coating, e.g., comprising gold and/or silver.

For some applications, and as shown in FIG. 5D, upper edge 94 of tissue-cutting element 90 forms lower surface 99 of hollow cavity 96. As described hereinabove, tissue-cutting element 90 is made from a highly absorptive material, having a low thermal mass and high thermal conductivity, that converts the laser energy to heat. It is therefore typically desirable that lower surface 99 has a low reflectivity. For example, for some applications, lower surface 99 reflects no more than 30 percent of the laser energy that reaches the lower surface.

The reflectivity of internal upper surface 100 is therefore typically higher than the reflectivity of lower surface 99. For some applications, given the same amount of laser energy that reaches internal upper surface 100 and lower surface 99, the internal upper surface reflects at least two times (e.g., at least three times) as much of the laser energy.

Thus, hollow cavity 96 acts as a hollow laser beam reflector that reflects the laser energy toward upper edge 94 of tissue-cutting element 90 (e.g., in a direction that is toward both the upper edge and lower edge 92 of the tissue-cutting element).

For some applications (as described hereinabove with reference to FIG. 2), when the surgeon operates mechanical cutting mechanism 38 using handle 22 (causing mechanical cutting blade 82 to pivot toward stabilizing base 86 and cut the tissue that is disposed between them), microswitch 56 connected to handle 22 operates laser 36 in generally simultaneous action with the actuation of mechanical cutting mechanism 38. For such applications, the mechanical cutting of the tissue begins at the same time the laser energy is radiated into hollow cavity 96. For some applications, laser 36 may be activated prior to the actuation of mechanical cutting mechanism 38 or following the actuation of mechanical cutting mechanism 38.

FIG. 5D depicts the laser energy inside hollow cavity 96, which reflects the laser optical energy toward tissue-cutting element 90, which in turn converts the laser energy into heat that is used to coagulate or vaporize the tissue that is in direct contact with the now-hot lower edge 92 of tissue-cutting element 90. In effect, the presence of the laser energy converts lower edge 92 of tissue-cutting element 90, which based on experiments carried out by the inventors would not be sharp enough to easily cut the tissue without the presence of the laser energy, into a hot, effectively sharp knife edge that facilitates rapid cutting and coagulation of tissue (i) using a lower mechanical force than would be required in the absence of the laser energy, and (ii) at a higher cutting rate than would be required to mechanically cut the tissue in the absence of the laser energy. Similarly, cutting mechanism 38 requires a lower level of laser energy than that which would be required to cut the tissue by using laser energy alone, in the absence of mechanical cutting. For example, in experiments conducted using laser energy in the absence of mechanical cutting, a 980 nm diode laser yielded 0.0027 mm3/joule, and a 1470 nm diode laser yielded 0.0035 mm3/joule of coagulated and/or vaporized tissue. By contrast, the same diode lasers each yielded 0.1 to 0.3 mm3/joule of coagulated and/or vaporized tissue when the laser energy was accompanied by mechanical cutting, as described herein.

FIGS. 5F-I respectively show solid and cross-sectional views of mechanical cutting blade 82 integrated into a modified embodiment of tip 32. As shown, mechanical cutting blade 82 pivots (e.g., from a position shown in FIGS. 5F-G) toward tissue-stabilizing base 86 (e.g., to a position shown in FIGS. 5H-I) around mechanical joint 84 (e.g., a pivot 102 thereof). For some applications, a distal end 104 (FIGS. 5G and 5I) of optical fiber 34 runs through the pivot 102 towards hollow cavity 96. Thus, pivot 102 guides optical fiber 34 such that the laser energy is delivered directly into hollow cavity 96. For some applications, an additional function of pivot 102 is to block scattered laser radiation from exiting hollow cavity 96.

Additionally, distal end 104 being fixed inside pivot 102 protects optical fiber 34 and enables mechanical cutting blade 82 to pivot without further bending optical fiber 34, i.e., as mechanical cutting blade 82 pivots, a distal-portion axis 63 of a distal portion 105 of optical fiber 34 remains at a generally constant angle to central longitudinal axis 46 of elongate shaft 26. Typically for such applications, the laser energy is emitted into cavity 96 at a fixed angle with respect to a distal-portion axis 63 (e.g., is emitted parallel to the distal-portion axis).

Reference is now made to FIGS. 6A-H, which depict the heat distribution along lower edge 92 of tissue-cutting element 90 as mechanical cutting blade 82 pivots from an open position (FIGS. 6A-D) to a closed position (FIGS. 6E-H), while laser energy 97 is being delivered to hollow cavity 96, in accordance with some applications of the present invention. FIGS. 6A and 6E show schematic illustrations of mechanical cutting blade 82 in an open position and a closed position, respectively, with respect to tissue-stabilizing base 86. FIGS. 6B and 6F are schematic illustrations of mechanical cutting blade 82 in the same open and closed positions respectively corresponding to FIGS. 6A and 6E, without showing the rest of tip 32, and optical fiber 34 entering mechanical cutting blade 82, e.g., through pivot 102. FIGS. 6C and 6G depict ray-tracing diagrams showing laser energy 97 inside hollow cavity 96 being reflected by internal upper surface 100 toward upper edge 94 of tissue-cutting element 90 in the same open and closed positions respectively corresponding to FIGS. 6A and 6E.

As described hereinabove with reference to FIGS. 5A-I, optical fiber 34 is typically positioned so as to emit laser energy 97 into hollow cavity 96 in a direction that is at a fixed angle with respect to distal-portion axis 63. In the configuration of tip 32 shown in FIGS. 6A-H, distal-portion axis 63 is generally parallel to longitudinal axis 46 of shaft 26. Distal portion 105 of optical fiber 34 therefore remains generally parallel to longitudinal axis 46 by being fixed inside pivot 102, regardless of the orientation of mechanical cutting blade 82. Laser energy 97 is therefore emitted into hollow cavity 96 from distal end 104 of optical fiber 34 in a direction that is generally parallel to longitudinal axis 46, regardless of the position of mechanical cutting blade 82 as it pivots toward tissue-stabilizing base 86 in order to cut the tissue. As a result, the positioning of internal upper surface 100 of hollow cavity 96, i.e., the positioning of the laser reflector, changes with respect to the direction of laser energy 97 as mechanical cutting blade 82 pivots downward. For some applications and as shown in FIGS. 6C and 6G, a laser reflection angle between distal-portion axis 63 and an upper surface plane defined by upper surface 100 becomes more obtuse as mechanical cutting blade 82 pivots downward. As described hereinbelow, laser reflection angle becoming more obtuse as mechanical cutting blade 82 pivots downward facilitates distribution of the laser energy along upper edge 94 of cutting blade 82, as cutting mechanism 38 is actuated.

FIG. 6C shows mechanical cutting blade 82 in a first position as it pivots toward tissue-stabilizing base 86, e.g., the open position corresponding to FIGS. 6A-B. FIG. 6D shows the heat distribution along lower edge 92 of tissue-cutting element 90 while mechanical cutting blade 82 is in the first position shown in FIG. 6C. In this first position, laser energy 97 is reflected toward a first location 106 along upper edge 94 of tissue-cutting element 90, and a corresponding first location 106' along lower edge 92 of tissue-cutting element 90 is shown as having been heated by the thermally conducted absorbed laser energy (FIG. 6D). FIG. 6G shows mechanical cutting blade 82 in a second position as it pivots toward tissue-stabilizing base 86, e.g., the closed position corresponding to FIGS. 6E-F. FIG. 6H shows the heat distribution along lower edge 92 of tissue-cutting element 90 while mechanical cutting blade 82 is in the second position shown in FIG. 6G. In this second position, laser energy 97 is reflected toward a second location 108, distal to first location 106, along upper edge 94 of tissue-cutting element 90, and a corresponding second location 108' along lower edge 92 of tissue cutting element 90 is shown as having been heated by the thermally conducted absorbed laser energy.

Thus, as mechanical cutting blade 82 pivots toward tissue-stabilizing base 86 in order to cut the tissue, the conducted heat starts at a proximal side of lower edge 92 (i.e., closer to pivot 102), and moves in a distal direction. As described hereinabove, laser 36 is typically activated at approximately the same time as mechanical cutting mechanism 38 is activated to cut the tissue. In this way, the surgeon can position tip 32 at a desired location and further position the desired tissue to be cut between mechanical cutting blade 82 and tissue-stabilizing base 86, prior to activating laser 36.

The heat distribution in a proximal-to-distal direction along lower edge 92 of tissue-cutting element 90 further enables heat from the laser energy 97 to be directed at the specific location along lower edge 92 that is actually cutting tissue. At the beginning of the cut, when mechanical cutting blade 82 is still in an open position, it is the proximal side of lower edge 92 that begins to cut the tissue and that is being heated by the absorbed laser energy. As mechanical cutting blade 82 pivots downwards, the tissue-cutting location moves distally along lower edge 92 of tissue-cutting element 90, as does the heat distribution.

The following are descriptions of two experiments carried out by the inventors using a stainless steel, hollow cavity light guide implementation of tool 20:

Experiment 3

The test was conducted using the following setup:
Laser type: diode array
Wavelength: 1470 nm
Laser power range: 7-45 W
Laser modulation: ranging from 100 microsecond-long pulses to continuous wave (CW) at 10-100% duty cycle
Beam Delivery: fiber optic 360 micrometer core 0.22 NA
Laser power test equipment: thermopile power meter (to test laser power)
Laser modulation test equipment: digital oscilloscope
Tested substrate: animal (pig) meniscus Laboratory Test Results of Experiment 3

1. Cutting of animal meniscus with the experimental setup using a hollow cavity metal blade without laser energy was not possible; the blade was not sharp enough to perform the cutting.
2. Cutting of animal meniscus with the experimental setup using a hollow cavity metal blade with laser energy resulted in successful smooth cutting and coagulation of the treated area using a blade edge force below 0.5 N, within the following average power ranges in saline-immersed conditions: 18 W CW, 25 W CW, and 30 W CW. It is noted that since in the experiment a fully metal blade (stainless steel, hollow-cavity blade) was used, the lateral edges of the blade also heated up and when the lateral edges touched the tissue, this created a carbonization effect. The inventors hypothesize that with body portion 98 of mechanical cutting blade 82 being made from a material with low thermal conductivity, as described hereinabove with reference to FIGS. 5A-I, the lateral edges of mechanical cutting blade 82 would not be heated. At 40 W of power, damage to the blade was observed.

Experiment 4

The test was conducted using the following setup:
Laser type: diode pumped solid state laser
Wavelength: 980 nm
Laser power range: 5-60 W
Beam Delivery: fiber optic 125 micrometer core
Laser power test equipment: thermopile power meter (to test laser power)
Tested substrate: animal (pig) meniscus Laboratory Test Results of Experiment 4

1. Cutting of animal meniscus with the experimental setup using a hollow cavity metal blade without laser energy was not possible; the blade was not sharp enough to perform the cutting.
2. Cutting of animal meniscus with the experimental setup using a hollow cavity metal blade with laser energy resulted in successful smooth cutting and coagulation of the treated area with low blade edge force, within the following average power ranges in saline immersed conditions: 18 W CW and 25 W CW. It is noted that since in the experiment a fully metal blade (stainless steel, hollow-cavity blade) was used, the lateral edges of the blade also were heated, and when the lateral edges touched the tissue a carbonization effect was created. The inventors hypothesize that with body portion 98 of mechanical cutting blade 82 being made from a material with low thermal conductivity, as described hereinabove with reference to FIGS. 5A-I, the lateral edges of mechanical cutting blade 82 would not be heated.

It is noted that while lasers of two specific wavelengths were used in the above experimental setups, as described hereinabove with reference to FIGS. 1A-B, laser 36 may emit laser energy at a wavelength of at least 300 nanometers and/or less than 3 micrometers, e.g., at a wavelength of at least 750 nanometers and/or less than 1500 nanometers, e.g., 980 nanometers or 1470 nanometers.

Reference is now made to FIGS. 7A-D, which are schematic illustrations of biter configurations for mechanical cutting mechanism 38, in accordance with some applications of the present invention. For some applications, moving part 40 of mechanical cutting mechanism 38 comprises a first jaw 110, and other part 42 of mechanical cutting mechanism 38 comprises a second jaw 112. First and second jaws 110 and 112 are coupled to each other at a jaw-hinge 114, such that mechanical cutting mechanism 38 cuts the tissue disposed between first jaw 110 and second jaw 112 as first jaw 110 pivots about the jaw-hinge 114 toward second jaw 112.

In a conventional meniscectomy, often many small tissue cuts are performed in order to obtain a larger curved cut of the meniscus. The inventors have realized, based on evaluation and analysis of typical meniscus tears, that the biter configurations of mechanical cutting mechanism 38 being able to generate a curved cut having an arc length of at least 6 mm and/or less than 20 mm in a single bite would allow most common meniscus tears to be treated in single or double bite, as opposed to many small bites. Thus, for some applications, first and second jaws 110 and 112 are curved such that second jaw 112 is placeable on a flat surface in a manner in which (a) first jaw 110 can articulate toward and away from the flat surface, and (b) the respective curves of first and second jaws 110 and 112 are in a plane that is parallel to the flat surface. FIGS. 7A-C show tip 32 in an orientation in which it would be placed on the flat surface. For some applications, the curve of first and second jaws 110 and 112 has a radius of curvature of at least 3 mm and/or less than 20 mm. FIG. 7D shows tip 32 of tool 20 making a curved cut in a meniscus 113 of a subject.

In this configuration, optical fiber 34 delivers the laser energy to tip 32 such that the laser energy leaves tip 32 and heats the tissue that is disposed between first jaw 110 and second jaw 112 by irradiating the tissue, e.g., by irradiating the tissue through a fluid that surrounds the tissue. Typically, optical fiber 34 delivers the laser energy to tip 32 via an optical light guide 116 that is disposed at least partially within tip 32 and directs the laser energy toward the tissue that is disposed between first jaw 110 and second jaw 112, in a similar manner as optical light guide 58 described hereinabove with reference to FIGS. 3A-B and 4A-C. Similarly to optical light guide 58, optical light guide 116 is made of a high-melting-point material, e.g., sapphire or diamond. Typically, optical fiber 34 is coupled to optical light guide 116 at a proximal end of optical light guide 116.

Similarly to optical light guide 58, optical light guide 116 has (i) an energy emitting surface 118 that interfaces with the tissue and (ii) at least one internal reflective surface. The internal reflective surface is disposed at an angle so as to reflect the laser energy from the optical fiber toward the tissue that is disposed between the first jaw and the second jaw. Thus, when the laser energy enters optical light guide 116, the laser energy is reflected toward energy emitting surface 118, which emits the laser energy to irradiate the tissue. When tissue is disposed between first jaw 110 and second jaw 112, energy-emitting surface 118 emits the laser energy that irradiates the tissue at the same time as mechanical cutting mechanism 38 cuts the tissue by first jaw 110 pivoting toward second jaw 112. As described hereinabove, the laser energy heats the tissue to a temperature of at least 50 degrees Celsius, e.g., at least 60 degrees Celsius and/or less than 65 degrees Celsius (alternatively or additionally between 60+/−5 degrees Celsius and 65+/− degrees Celsius) so as to coagulate the irradiated tissue as it is cut.

FIG. 7A shows a configuration of optical light guide 116 in which energy emitting surface 118 is sharp, such that energy emitting surface 118 itself acts as a knife that is pressed against the tissue as first jaw 110 pivots toward second jaw 112. FIG. 7B shows a configuration of optical light guide 116 in which energy emitting surface 118 is blunt. In this configuration, the tissue is cut by the biting action of first jaw 110 pivoting toward second jaw 112. FIG. 7C shows a configuration of tip 32 in which a tooth 119 of first jaw 110 enters a slot 121 in second jaw 112 as the first jaw pivots toward second jaw 112. In this configuration, energy emitting surface 118 of optical light guide 116 is a side-facing surface that is disposed along a lateral edge of slot 121. It is noted that while FIG. 7C depicts tooth 119 of first jaw 110 entering slot 121 in second jaw 112, this is a non-limiting example. Alternatively or in addition, the first jaw may define a slot, and the second jaw 112 may have a tooth that enters the slot in the first jaw as the first jaw pivots toward the second jaw.

It is also noted that FIGS. 7A-C depict optical light guide 116 as being disposed along second jaw 112 and having the same curve as the second jaw 112. This is a non-limiting example and, for some applications, optical light guide 116 is disposed along first jaw 110, i.e., along the moving jaw, and has the same curve as first jaw 110.

For some applications, alternatively to delivering the laser energy via an optical light guide, optical fiber 34 is positioned such that, during the surgical procedure, at least a distal portion of the optical fiber is in contact with the tissue that is disposed between first jaw 110 and second jaw 112. Typically for such applications, optical fiber 34 is configured to deliver the laser energy directly to the tissue by emitting the laser energy from a lateral edge of the distal portion of the optical fiber (configuration not shown). For some such applications, optical fiber 34 is disposed along first jaw 110. For some such applications, optical fiber 34 is disposed along second jaw 112.

Figure 8A:
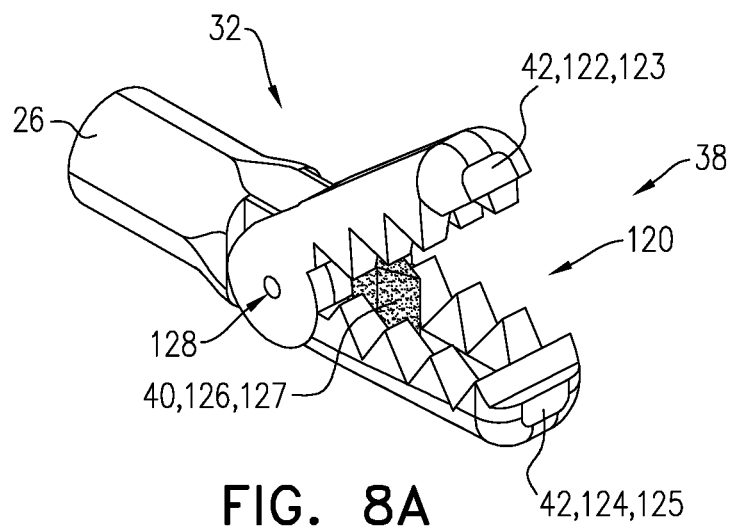
FIGS. 8A-B are schematic illustrations of a grasper configuration for the tip of the surgical tool, in accordance with some applications of the present invention.
Figure 8B:
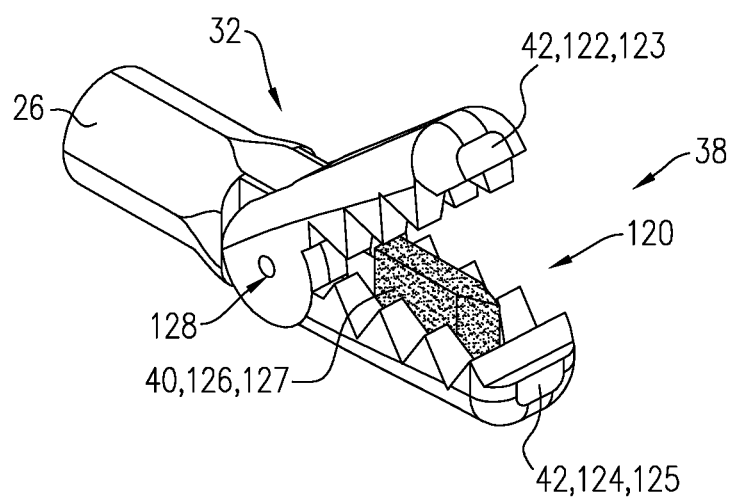

Reference is now made to FIGS. 8A-B, which are schematic illustrations showing a grasper configuration for mechanical cutting mechanism 38, in accordance with some applications of the present invention. For some applications, other part 42 of mechanical cutting mechanism 38 is a grasper 120 (a) having a first grasping element 122 and a second grasping element 124, and (b) configured to grasp tissue of the subject that is disposed between first grasping element 122 and second grasping element 124. Moving part 40 of mechanical cutting mechanism 38 is a mechanical cutting blade 126 disposed within grasper 120 that slides with respect to grasper 120 in order to cut the grasped tissue.

For some applications, first and second grasping elements 122 and 124 are a first and second jaw 123 and 125, respectively (as shown in FIGS. 8A and 8B). First jaw 123 and second jaw 125 are coupled to each other at a jaw-hinge 128, and grasper 120 grasps the tissue of the subject between first jaw 123 and second jaw 125.

For some applications and as shown, first jaw 123 is a moving jaw and second jaw 125 is a stationary jaw, such that the first jaw pivots about jaw-hinge 128 toward the second jaw. For some such applications, mechanical cutting blade 126 is disposed within second jaw 125, and slides longitudinally with respect to the second jaw to cut the tissue that is grasped between first jaw 123 and the second jaw. Alternatively, for some applications, mechanical cutting blade 126 is disposed within first jaw 123, i.e., the moving jaw (configuration not shown), and slides longitudinally with respect to the first jaw to cut the tissue that is grasped between the first jaw and second jaw 125. FIG. 8A shows mechanical cutting blade 126 in a fully retracted position, and FIG. 8B shows the mechanical cutting blade in its fully extended position.

For some applications, the laser energy is delivered to the grasper tip such that the laser energy leaves tip 32 and heats the tissue that is disposed between mechanical cutting blade 126 and grasper 120 by irradiating the tissue, e.g., by irradiating the tissue through a fluid that surrounds the tissue. As described hereinabove, the laser energy heats the tissue to a temperature of at least 50 degrees Celsius, e.g., at least 60 degrees Celsius and/or less than 65 degrees Celsius (alternatively or additionally between 60+/−5 degrees Celsius and 65+/− degrees Celsius), so as to coagulate the irradiated tissue, i.e., the cut tissue. For some applications, this is implemented by mechanical cutting blade 126 being an optical light guide 127, such as optical light guide 58 described hereinabove with reference to FIGS. 3A-B and 4A-C, coupled to a distal end of optical fiber 34, and configured to direct the laser energy toward the tissue that is disposed between mechanical cutting blade 126 and grasper 120. Similarly to optical light guide 58, optical light guide 127 comprises at least one internal reflective surface that is disposed at an angle so as to reflect the laser energy from optical fiber 34 toward the tissue, e.g., at an angle of at least 10 degrees and/or less than 41 degrees with respect to central longitudinal axis 62 of optical fiber 34. Similarly to optical light guide 58, optical light guide 127 is made of a high-melting-point material, e.g., sapphire or diamond.

For some applications, in contrast to laser irradiation of the tissue, mechanical cutting blade 126, or at least a portion of mechanical cutting blade 126, is configured to absorb the laser energy and thermally conduct the absorbed energy to the tissue by contacting the tissue that is disposed between mechanical cutting blade 126 and grasper 120. As described hereinabove, this is implemented by mechanical cutting blade 126, or at least the portion of mechanical cutting blade 126 being highly absorptive and having low thermal mass and high thermal conductivity. Upon thermally conducting the absorbed energy to the tissue, mechanical cutting blade 126, or at least the portion of the mechanical cutting blade, either coagulates or vaporizes the cut tissue.

For some applications, the effect of the laser energy on the tissue is implemented using a combination of tissue irradiation and thermal conduction of absorbed laser energy by direct contact with the tissue. This is achieved by using an optical light guide, such as optical light guide 58 (in the configuration of tip 32 shown in FIGS. 4A-C), optical light guide 116 (in the configuration of tip 32 shown in FIGS. 7A-C), or optical light guide 127 (in the configuration of tip 32 shown in FIGS. 8A and 8B), and putting a coating on the optical light guide, e.g., a coating on the energy-emitting surface of the optical light guide, that is configured to absorb at least some of the laser energy and thermally conduct the absorbed energy to the tissue that is disposed between moving part 40 and other part 42 of mechanical cutting mechanism 38. In this manner, some of the laser energy is emitted from the energy-emitting surface of the optical light guide (e.g., energy-emitting surface 64 in FIGS. 4A-B, and energy-emitting surface 118 in FIGS. 7A-C), and some of the energy is thermally conducted to the tissue via direct contact with cutting blade 126. For some applications, the coating on the optical light guide may be, for example, manganese dioxide ($MnO_2$).

Figure 9A:
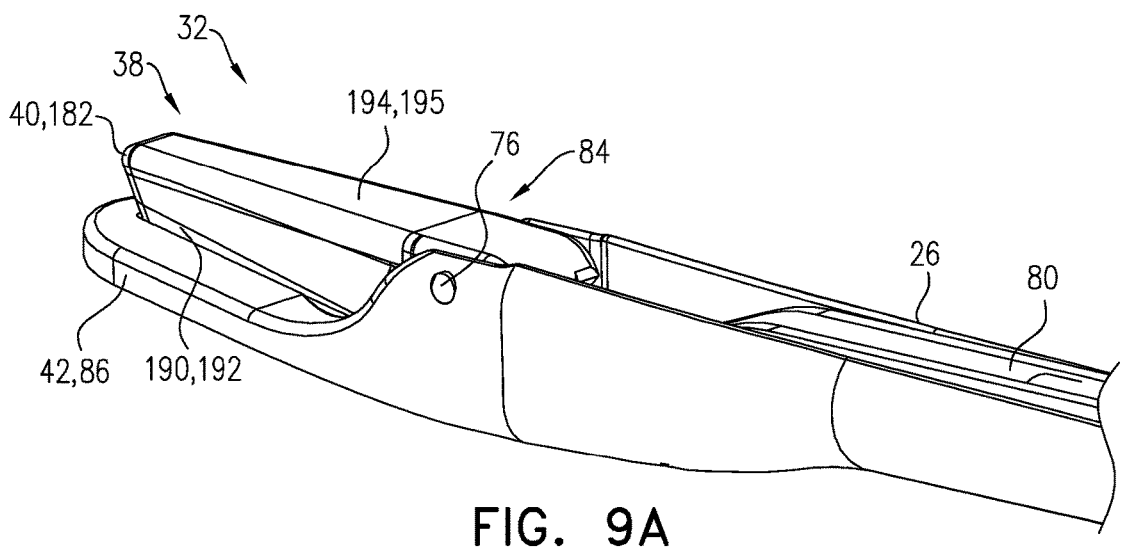
FIGS. 9A-C are schematic illustrations of a configuration of the tip of the surgical tool, in accordance with some applications of the present invention.
Figure 9B:
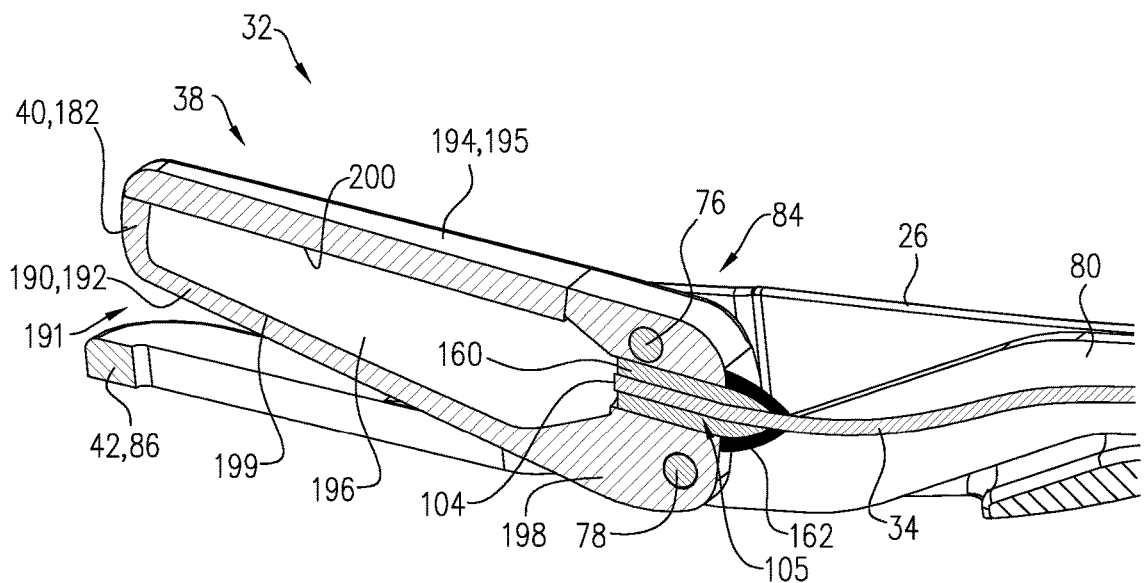
Figure 9C:
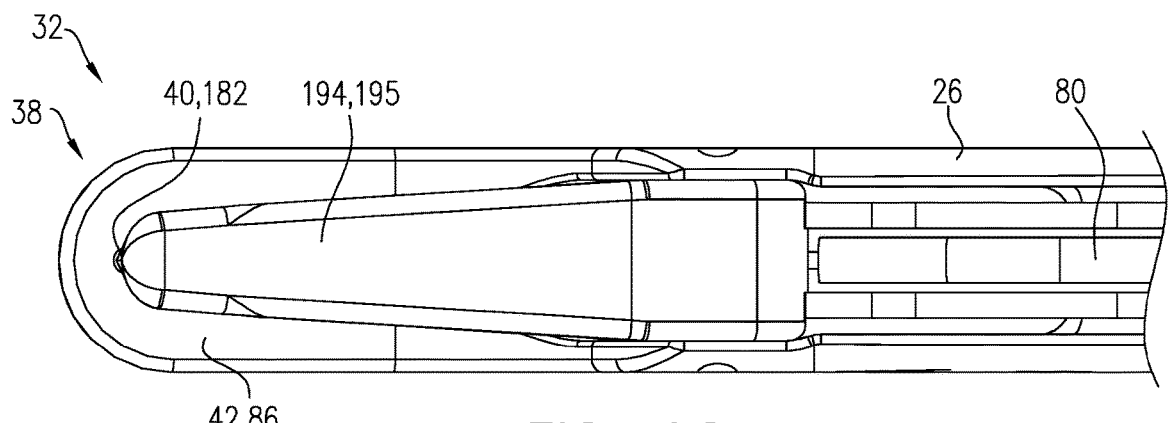

Reference is made to FIGS. 9A-C, which are schematic illustrations showing tip 32, in accordance with some applications of the present invention.

Except where noted, the configuration of tip 32 shown in FIGS. 9A-C (comprising a mechanical cutting blade 182) is typically similar to the configuration of the tip described hereinabove with reference to FIGS. 5A-I (comprising mechanical cutting blade 82). For example, moving part 40 of mechanical cutting mechanism 38 comprises mechanical cutting blade 182 that is coupled to tip 32 at mechanical joint 84, and other part 42 of mechanical cutting mechanism 38 is tissue-stabilizing base 86 that is configured to stabilize the tissue disposed between mechanical cutting blade 182 and tissue-stabilizing base 86, as the mechanical cutting blade cuts the tissue by pivoting toward tissue-stabilizing base 86.

Further similarly to cutting blade 82, in cutting blade 182, mechanical joint 84 includes pivot 76 around which mechanical cutting blade 182 pivots. Second pivot 78 is coupled to mechanical actuator 80 that moves longitudinally back and forth with respect to shaft 26 upon activation by handle 22, in order to cause mechanical cutting blade 182 to pivot.

Given the similarities between mechanical cutting blades 82, 182, the description below focuses upon features that are particular to cutting blade 182.

Cutting blade 182 is hollow, and is shaped to define a hollow cavity 196, such that the laser energy is emitted from fiber 34 into the hollow cavity in the interior of the cutting blade. As shown in FIG. 9B, a lower portion 191 of cutting blade 182 therefore defines an internal lower surface 199 of hollow cavity 196.

Typically, an internal upper surface 200 of hollow cavity 196 has a high reflectivity, in order to direct the laser energy toward lower portion 191. For some applications and as shown, upper surface 200 of hollow cavity 196 and an upper edge 194 of cutting blade 182 are defined by an upper plate 195 of the cutting blade. For example, a portion of upper plate 195 may comprise stainless steel and/or chromium, and upper surface 200 may comprise a reflective coating, e.g., gold and/or silver.

In mechanical cutting blade 182, distal portion 105 of optical fiber 34 is circumferentially surrounded by a ceramic sleeve 160 (FIG. 9B). At least a portion of ceramic sleeve 160 is disposed within a tissue-cutting element 190 (e.g., within a body portion 198 thereof). In this way, ceramic sleeve 160 thermally insulates distal portion 105 of optical fiber 34 from cutting element 190. For some such applications, distal end 104 (e.g., at least 0.2 mm and/or less than 1.0 mm at the distal end of fiber 34) protrudes from ceramic sleeve 160, in order to avoid interference by ceramic sleeve 160 with the laser energy leaving fiber 34.

For some applications and as shown, an adhesive 162 (e.g., an epoxy or other ceramic glue, such as EPO-TEK (R) manufactured by Epoxy Technology, Inc., Billerica, Mass.) is applied to a proximal portion of ceramic sleeve 160, in a manner that forms a watertight seal between: (i) the ceramic sleeve and tissue-cutting element 190, and (ii) distal portion 105 of optical fiber 34 and the ceramic sleeve. The watertight seal facilitates proper functioning of laser 36 and tip 32 by preventing entry of fluid (e.g., body fluid or saline in which the tip may be immersed during use) to hollow cavity 196.

Figure 10:
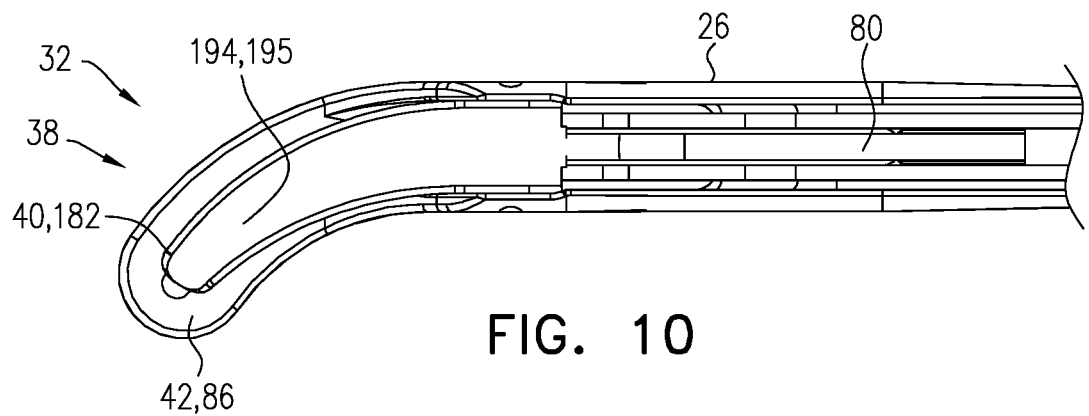
FIGS. 10-11 are schematic illustrations of alternate configurations of the tip of the surgical tool, in accordance with some applications of the present invention.
Figure 11:
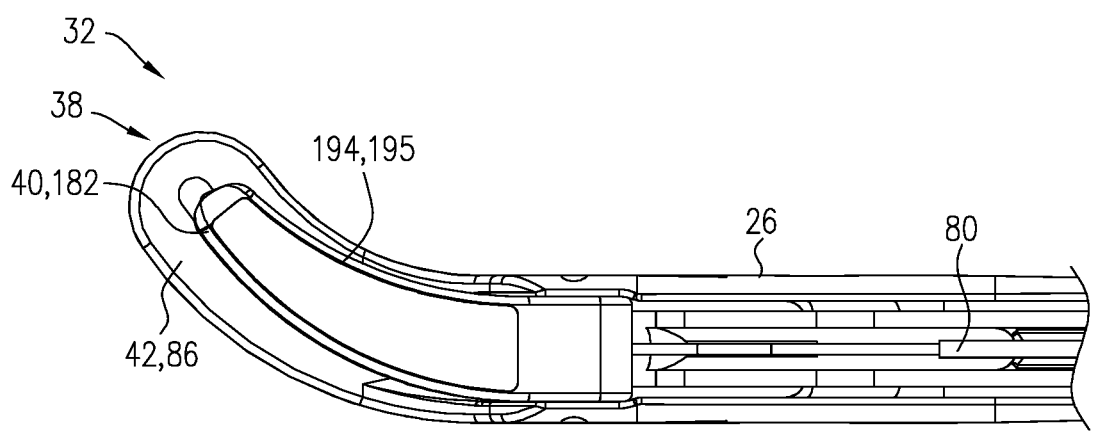

Reference is made to FIGS. 10-11, which are schematic illustrations of alternate configurations of tip 32, in accordance with some applications of the present invention.

FIGS. 10-11 are top-views of curved configurations of tip 32 that are otherwise generally similar to the straight tip configuration described hereinabove with reference to FIGS. 9A-C. FIGS. 10-11 show respective tips 32 having different curvatures, each curvature being suited for approaching a target tissue differently. All of the tips 32 are shown in an orientation in which, were they to be placed on a flat surface, the respective curves of the cutting blade 182 and stabilizing base 86 would be in a plane that is parallel to the flat surface, and cutting blade 182 would articulate toward and away from the flat surface. In this orientation, when viewed from a proximal portion of shaft 26, tip 32 shown in FIG. 10 curves to the left, whereas the tip shown in FIG. 11 curves to the right.

As described hereinabove with reference to FIGS. 7A-D, a curved cut having an arc length of at least 6 mm and/or less than 20 mm (and/or having a radius of curvature of at least 3 mm and/or less than 20 mm) would allow many common meniscus tears to be treated. In order to facilitate such a curved cut, the configurations of tip 32 shown in FIGS. 10-11 are shaped such that respective cutting mechanisms 38 thermally conduct absorbed laser energy to a curved portion of tissue that is disposed between the curved cutting blade 182 and the curved stabilizing base 86.

Reference is made to FIGS. 12A-C and 13A-D, which are schematic illustrations showing use of the configuration of tip 32 of surgical tool 20 shown in FIGS. 9A-C, in accordance with some applications of the present invention.

FIGS. 12A-B show a schematic cross-sectional view of cutting blade 182, before (FIG. 12A) and during (FIG. 12B) delivery of laser energy 97 from distal end 104 of optical fiber 34, into hollow cavity 196.

Typically, and as shown in FIG. 12B, the laser energy 97 is not actively directed (e.g., using a lens or other optical element) toward a specific portion of hollow cavity 196. Rather than actively directing laser energy 97 via an optical element, the respective optical properties (e.g., reflectivity or absorption of the laser energy) of different portions of cutting element 190 facilitate absorption of the laser energy by lower portion 191, in which the laser energy is transformed into heat that heats the lower portion (e.g., lower edge 192 thereof).

Typically for such applications, upper surface 200 of cavity 196 is a reflective coating (e.g., comprising gold and/or silver). Thus, laser energy 97 that reaches upper surface 200 is typically not absorbed by the upper surface, but is reflected (e.g., toward lower portion 191). Accordingly, internal lower surface 199 comprises a highly absorptive material, having a low thermal mass and high thermal conductivity (e.g., tungsten, such as an alloy comprising tungsten), that converts the laser energy to heat, which is conducted to lower edge 192.

For some applications, respective textures of upper surface 200 and lower surface 199 contribute to (i) reflection of the laser energy by the upper surface and (ii) absorption of the laser energy by the lower surface. Typically for such applications, upper surface 200 has a texture that is smoother than a texture of lower surface 199. For example, lower surface 199 may define a microtexture and/or a plurality of microperforations.

In this way, laser energy 97 is directed toward internal lower surface 199 of hollow cavity 196, and is conducted as heat to lower edge 192 of tissue-cutting element 190. Directing energy toward lower edge 192 of tissue-cutting element 190 as described hereinabove enables use of relatively low levels of laser energy to heat the lower edge of the cutting element. That is, without the described differences in absorption and reflection between upper surface 200 and lower surface 199, more laser energy would have to be delivered from optical fiber 34 in order to heat lower edge 192 to the same temperature. Another advantage of directing the energy to lower edge 192 lies in not excessively heating other areas of tissue-cutting element 190 (e.g., body portion 198 thereof), thereby limiting a scope of the heat-affected zone of tissue.

The lower portion of FIG. 12C is a schematic representation of a thermal photograph 182' showing distribution of heat 101' along mechanical cutting blade 182. Thermal photograph 182' was recorded shortly after actuating laser 36.

The graph in the upper frame of FIG. 12C displays the temperature to which tissue cutting blade 182 was heated, along a portion of a blade-height axis 220. The x-axis of the graph extends from below lower portion 191' that corresponds to lower portion 191 of cutting element 190, to above upper edge 194' that corresponds to upper edge 194 of the cutting element. As shown, the lowest part of lower portion 191 was heated to between 25 and 27 degrees Celsius. Above this lowest part, a hottest portion of the cutting blade 182 was heated to about 43 degrees. The hottest portion of cutting blade 182 was closer to lower portion 191 than to upper edge 194.

The graph in the middle frame of FIG. 12C represents the temperature to which the tissue cutting blade 182 was heated, along a portion of a blade-length axis 222 that transverses lower portion 191', from a proximal portion 187' to a distal portion 189' of thermal photograph 182'. As shown, most of the length of lower portion 191 was heated to a mean temperature of over 41 degrees Celsius.

Figure 13B:
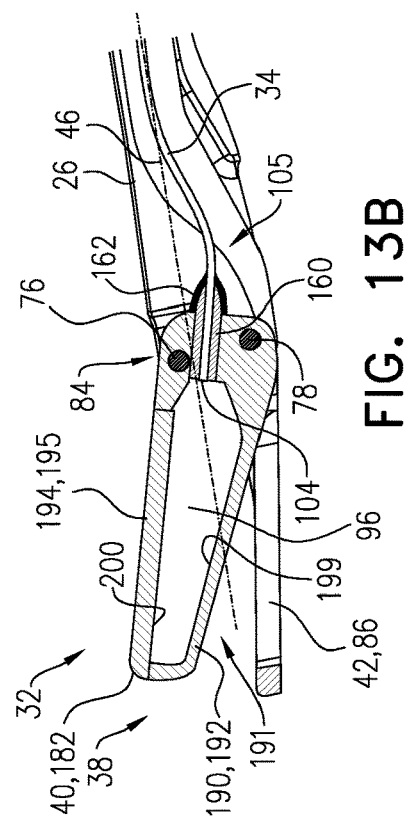
Figure 13D:
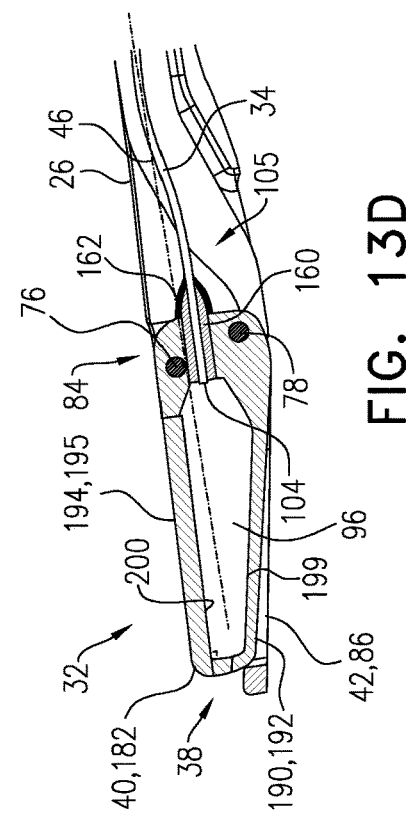
Figure 13A:
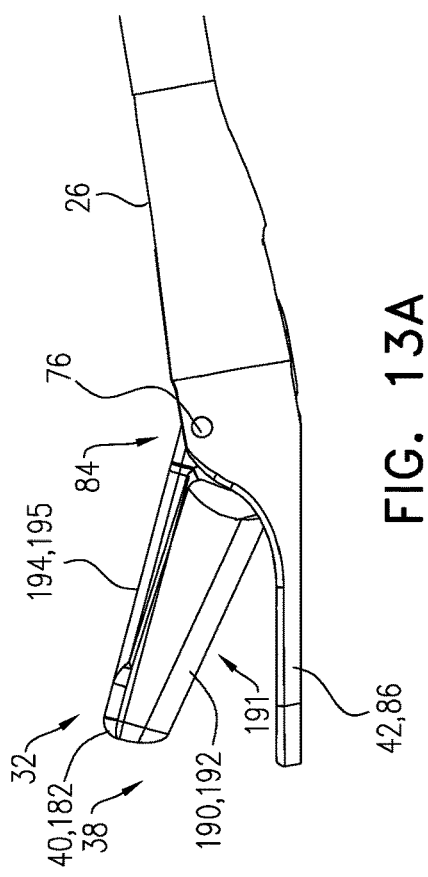
Figure 13C:
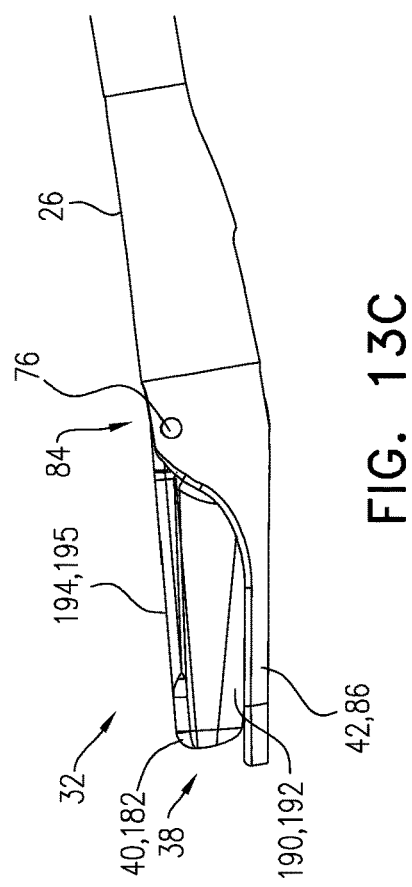

FIGS. 13A-D show solid and cross-sectional views of the configuration of tip 32 shown in FIGS. 9A-C, in which mechanical cutting blade 182 is in an open (elevated) position (FIGS. 13A-B) and in a closed (lowered) position (FIGS. 13C-D). As shown, mechanical cutting blade 182 pivots from the open position, toward tissue-stabilizing base 86 (e.g., to the closed position) around mechanical joint 84 (e.g., pivot 76 thereof).

For some applications and as shown in FIGS. 13B and 13D, distal portion 105 of optical fiber 34 does not necessarily remain at a constant angle with respect to central longitudinal axis 46 while mechanical cutting blade 182 pivots. Instead, distal portion 105 (e.g., part of the distal portion that is proximal of adhesive 162) is bent with respect to longitudinal axis 46 as mechanical blade pivots into the open position (FIG. 13B).

For some applications, adhesive 162 is shaped to provide mechanical support to distal portion 105 of optical fiber 34 as mechanical blade 182 pivots. For some such applications, adhesive 162 may have a greater flexibility than ceramic sleeve 160 or body portion 198 of mechanical cutting blade 182. Therefore, while distal portion 105 of optical fiber 34 is bent with respect to longitudinal axis 46 (FIG. 13B), adhesive 162 at least partially conforms to the bending. The flexibility of adhesive 162 prevents sharp bending of the portion of optical fiber 34 that exits the more rigid ceramic sleeve 160 or body portion 198, as mechanical blade 182 pivots.

For some applications, and as shown in FIGS. 12A-B, optical fiber 34 is supported by a coating 33 (e.g., comprising ethylene-tetrafluoroethylene) that mechanically supports optical fiber 34. Typically for such applications, the mechanical support that is provided by coating 33 facilitates protection of the structural integrity of optical fiber 34 while distal portion 105 thereof is bent. Since mechanical cutting blade 182 (e.g., body portion 198 thereof) is heated while laser energy 97 is delivered from optical fiber into hollow cavity 196, ceramic sleeve 160 thermally isolates both fiber 34 and coating 33 from the cutting blade, thereby preventing melting of the coating and/or thermal damage to the fiber.

Reference is made to FIGS. 14A-D, which are schematic illustrations of a configuration for shape-changing region 44 of shaft 26, in accordance with some applications of the present invention.

Figure 14A:
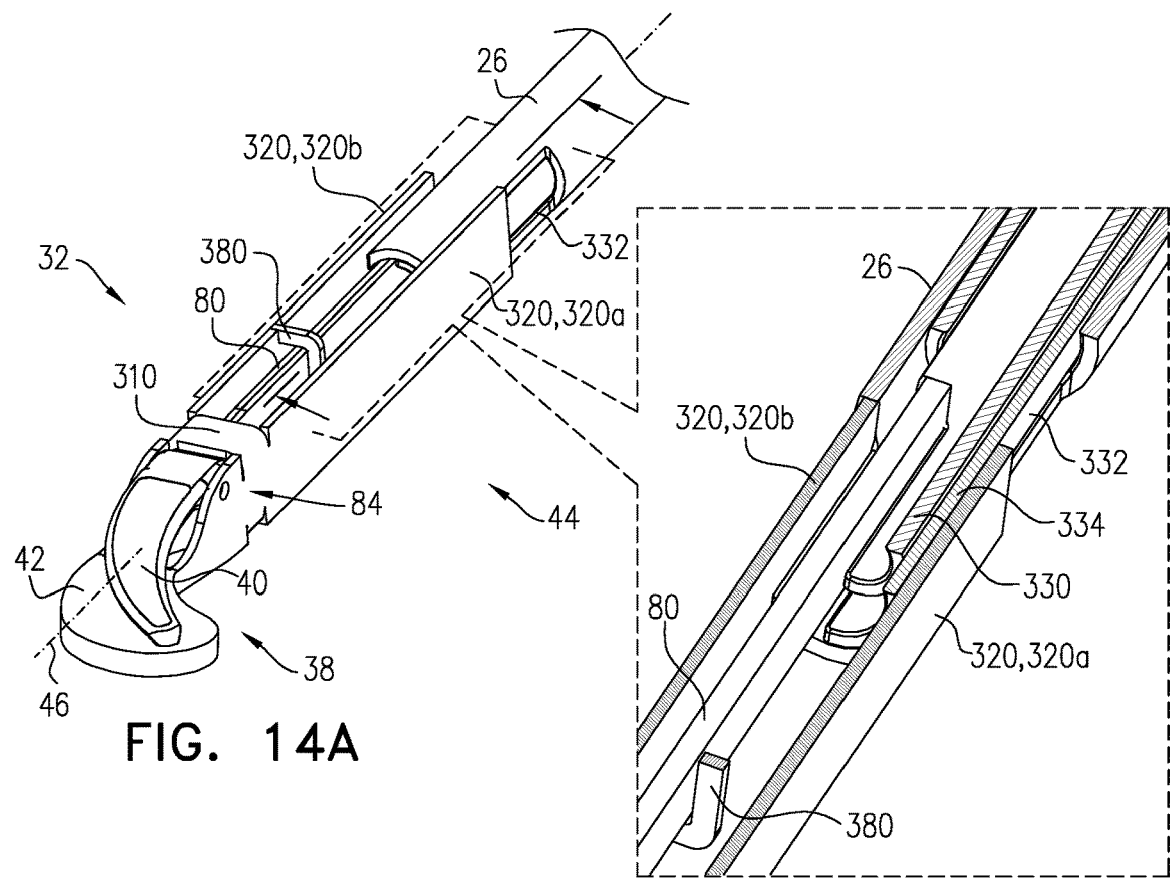

For some applications, shape-changing region 44 may be implemented as comprising one or more side-plates 320, e.g., a pair of side-plates as shown in FIG. 14A. Similarly to the configuration of shape-changing region 44 described hereinabove with reference to FIG. 1C, side-plates 320 are typically more flexible in a first plane than in a second plane that is perpendicular to the first plane. For some such applications, side-plate 320 is generally planar, and a side-plate plane defined by the side-plate is the second plane in which the side-plate is less flexible. Since longitudinal axis 46 of shaft 26 typically lies in the first plane, side-plate 320, and therefore shape-changing region 44 in general, is articulatable laterally, as shown in FIGS. 14C-D.

As provided by some applications of the present invention, an advantage of this configuration of shape-changing region 44 lies in its narrow profile, which facilitates less traumatic access to a target tissue. Typically, a widest part of shape-changing region 44 has a longest width W1 in a cross-section perpendicular to longitudinal axis 46 that is less than 3 mm.

The narrow profile of shape-changing region 44 is at least partially facilitated by the orientation of side-plate 320. That is, side-plate 320 typically does not need to be thick in order to resist bending along the side-plate plane. This feature grants shape-changing region 44 substantial rigidity along the side-plate plane, despite the side-plate typically having a greatest thickness of between 0.1 and 0.5 mm (e.g., less than 0.3 mm).

As shown in FIG. 14A, shaft 26 that comprises shape-changing region 44 is otherwise similar to configurations of the tip described hereinabove. That is, mechanical cutting mechanism 38 that comprises moving part 40 (e.g., cutting blade) and other part (e.g., cutting surface) 42 is coupled at mechanical joint 84 to mechanical actuator 80 that extends distally from within shaft 26.

As shown in FIG. 14A, mechanical actuator 80 of shape-changing region 44 is typically oriented, similarly to side-plate 320, such that the mechanical actuator has a thickness that is less than a height of the mechanical actuator that is generally parallel with the side-plate plane. Mechanical actuator 80 is therefore, like side-plate 320, typically more flexible along the first plane than along the side-plate plane. For some such applications, an actuator clip 380 that is affixed to at least one side-plate 320, and to mechanical actuator 80, facilitates passive deflection of the mechanical actuator, together with the side-plates.

For some applications it may be desirable to prevent unintended flexing of the side-plate, and therefore of shape-changing region 44. Therefore, in the shown configuration, a connecting portion 310 connects the respective distal portions of side-plates 320, and a proximal portion of the side-plates is operatively coupled to an articulation actuator 330 that extends distally (e.g., within an articulation actuator shaft 334) to shape-changing region 44. In this way, side-plates 320 are supported at both proximal and distal portions thereof, reducing a risk of inadvertent articulation of shape-changing region 44.

For some applications, and as shown, shape-changing region 44 comprises a pair of side-plates 320. For some such applications, each side-plate 320 may be actuatable using articulation actuator 330. For some applications, and as shown, one side-plate is an actuatable side-plate 320a, and the other side-plate is a non-actuatable side-plate 320b.

For some applications, and as shown, the difference between actuatable side-plate 320a and non-actuatable side-plate 320b may depend upon the manner in which each side-plate interacts with (e.g., is coupled to) shaft 26. For example, and as shown in the inset of FIG. 14A, non-actuatable side-plate 320b may be fixedly coupled to (e.g., may abut) shaft 26. In contrast, actuatable side-plate 320a is slidably coupled to an articulation actuator track 332 at a distal portion of shaft 26. For this example, articulation of shape-changing region 44 occurs as a result of a user actuating articulation actuator 330 (e.g., pulling a proximal portion thereof), which causes side-plate 320a to slide along articulation track 332.

Figure 14B:
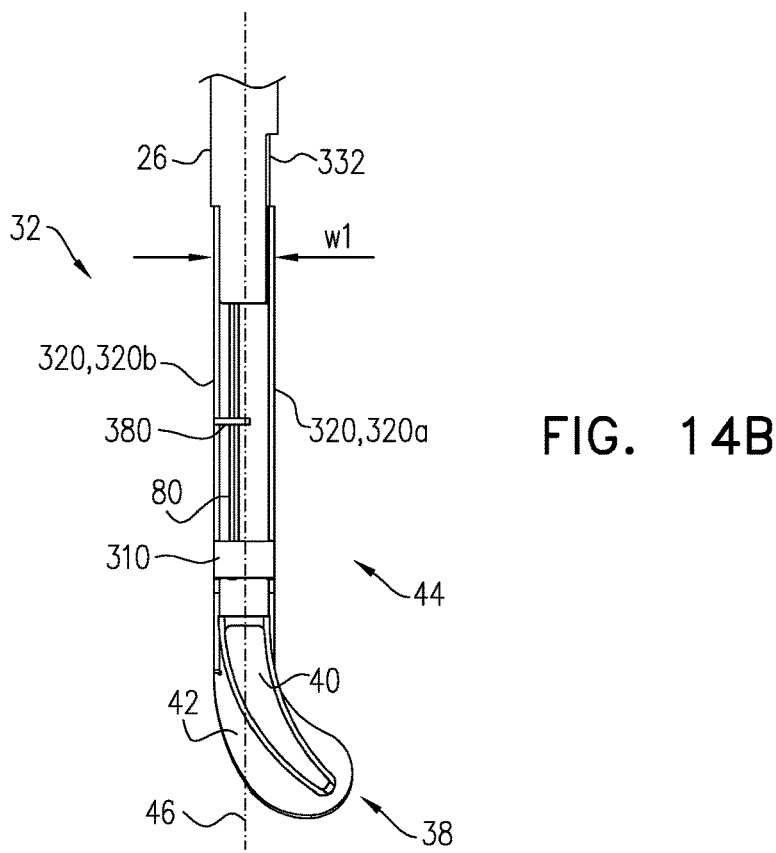

Comparison of shape-changing region 44 in a relaxed state (FIG. 14B) and in two different deflected states (14C-D) demonstrates the effect that sliding side-plate 320a along articulation track 332 has upon the orientation of shape-changing region 44. As shown in FIG. 14B, in the relaxed state, proximal ends of each side-plate 320 are located at approximately the same point along longitudinal axis 46, and each side plate, as well as shape-changing region 44 as a whole, are generally parallel with the longitudinal axis. In FIG. 14C, side-plate 320a has been pulled proximally (e.g., by pulling on articulation actuator 330) such that side-plate 320a flexes, causing shape-changing region 44, to articulate approximately 30 degrees. In FIG. 14D, side-plate 320a has been pushed proximally (e.g., by pushing on articulation actuator 330), causing shape-changing region 44, and with it tip 32, to articulate approximately 30 degrees in the opposite direction. For some applications, flexing side-plate 320 articulates shape-changing region 44 to an angle of up to 35 degrees with respect to longitudinal axis 46. For some applications, shape-changing region 44 has a bend radius that is less than 30 mm.

Non-actuatable side-plate 320b is typically passively deflected upon actuation of actuatable side-plate 320a. Side-plates 320 are therefore typically sufficiently flexible for actuation of one of the side-plates to passively deflect the other side-plate.

Reference is made to FIGS. 15A-D, which are schematic illustrations showing steps in preparation of a portion of the configuration of shape-changing region 44 shown in FIGS. 14A-D, in accordance with some applications of the invention.

Figure 15A:
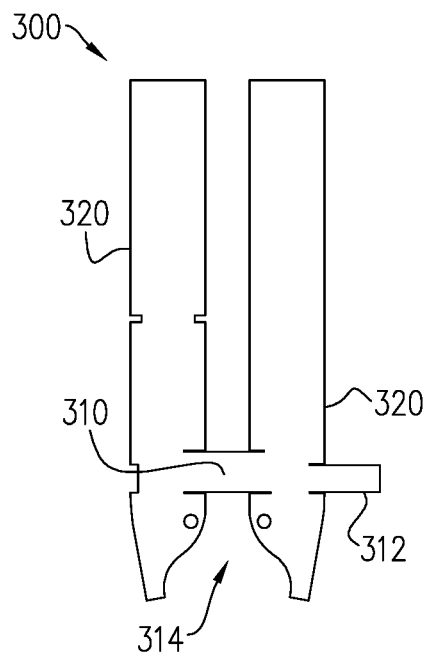
FIGS. 15A-D are schematic illustrations showing steps in preparation of a portion of the configuration of the shape-changing region shown in FIGS. 14A-D, in accordance with some applications of the invention.
Figure 15B:
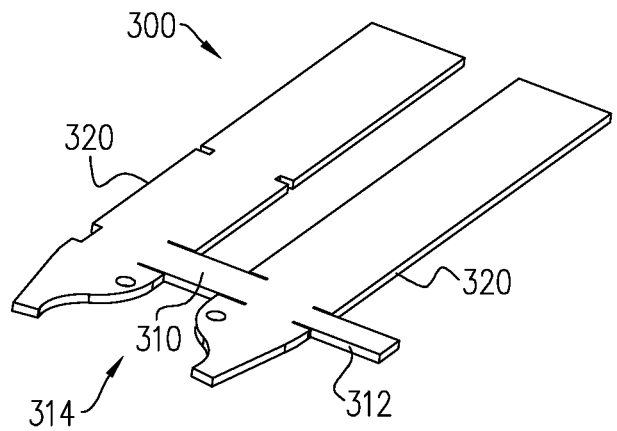
Figure 15C:
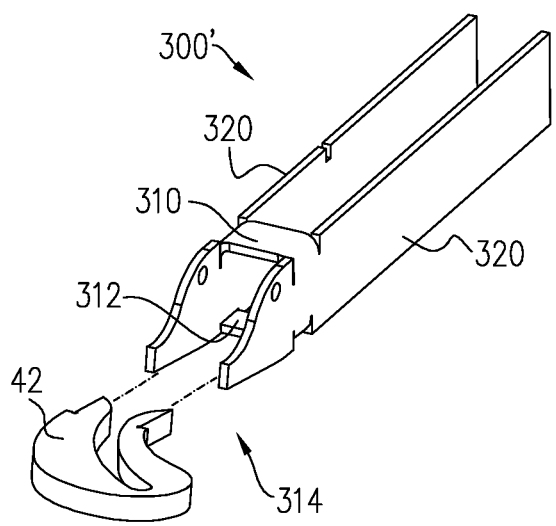
Figure 15D:
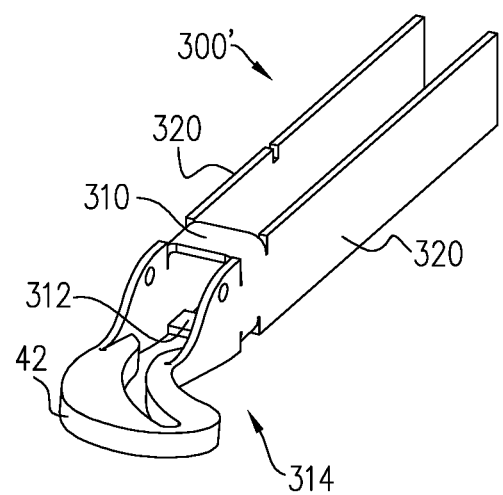

FIGS. 15A-B show a side-plate sheet 300 (e.g., made from sheet metal) comprising a pair of side-plates 320 that are joined by connecting portion 310. FIG. 15C shows side-plate sheet 300' having been processed such that each side-plate 320 is bent at an angle of approximately 90 degrees with relation to connecting portion 310. In this way, connecting portion 310, together with a spacer 312, stabilizes a distance between respective distal ends of side-plates 320. As shown in FIGS. 15C-D, the processing of side-plate sheet 300' prepares a distal portion 314 of the side-plate sheet to receive cutting surface 42.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use in a surgical procedure, the apparatus comprising:
   a tool comprising:
      a handle at a proximal end of the tool;
      an elongate shaft extending in a distal direction from the handle, the elongate shaft having proximal and distal portions;
      a tip disposed at the distal portion of the shaft, the distal portion of the shaft being sized and shaped to be inserted into a subject during a surgical procedure and to contact tissue of the subject; and
      an optical fiber configured to deliver laser energy to the tip,
   wherein:
      the tip further comprises a mechanical cutting mechanism comprising a moving part that:
         moves with respect to another part in order to cut tissue of the subject that is disposed between the parts, and
         is configured to absorb the laser energy and thermally conduct the absorbed energy to the tissue by contacting the tissue that is disposed between the parts; and
      the mechanical cutting mechanism is configured to cut the tissue of the subject using a mechanical force that is lower than a mechanical force that would be required to cut the tissue in the absence of the thermally conducted absorbed energy,
   wherein:
      the moving part of the mechanical cutting mechanism comprises a mechanical cutting blade that is coupled to the tip at a mechanical joint;
      the other part of the mechanical cutting mechanism is a tissue-stabilizing base configured to stabilize the tissue disposed between the mechanical cutting blade and the tissue-stabilizing base as the mechanical cutting blade cuts the tissue by pivoting toward the tissue-stabilizing base;
      at least a portion of the mechanical cutting blade is a tissue-cutting element that is configured to absorb the laser energy and thermally conduct the absorbed energy to the tissue by contacting the tissue that is disposed between the mechanical cutting blade and the tissue-stabilizing base, the tissue-cutting element:
         (a) having low thermal mass and high thermal conductivity, and
         (b) having a lower portion defining a lower edge that is configured to face the tissue, and an upper edge opposite the lower edge that faces away from the tissue;

the mechanical cutting blade is shaped to define a hollow cavity, the hollow cavity having an internal surface with high reflectivity;

the optical fiber is positioned so as to emit the laser energy into the hollow cavity; and the internal surface of the hollow cavity is shaped so as to reflect the laser energy toward the lower edge of the tissue-cutting element of the mechanical cutting blade.

2. The apparatus according to claim 1, further comprising a laser configured to generate the laser energy.

3. The apparatus according to claim 1, wherein the distal portion of the elongate shaft comprises a shape-changing region that is configured to change shape during the surgical procedure.

4. The apparatus according to claim 3, wherein a widest part of the shape-changing region has a cross-section perpendicular to a longitudinal axis of the shape-changing region, the cross-section having a width of less than 3 mm.

5. The apparatus according to claim 3, wherein the shape-changing region is configured to change shape under active control by the handle.

6. The apparatus according to claim 3, wherein the shape-changing region is configured to change shape more in a first plane than in a second plane perpendicular to the first plane.

7. The apparatus according to claim 6, further comprising an actuator that extends distally to the shape-changing region, wherein:

the shape-changing region comprises a side-plate, the side-plate:

having a relaxed state and a deflected state, and the actuator is operatively coupled to the side-plate such that actuation of the side-plate by the actuator causes the side-plate to flex along the first plane, such that the side-plate transitions from the relaxed state to the deflected state.

8. The apparatus according to claim 1, wherein:

the internal surface of the hollow cavity with high reflectivity is an internal upper surface of the tissue-cutting element, and the lower portion of the tissue-cutting element defines an internal lower surface of the hollow cavity, and the internal upper surface of the hollow cavity is shaped so as to reflect the laser energy in a direction that is toward:

the internal lower surface of the hollow cavity, and the lower edge of the tissue-cutting element.

9. The apparatus according to claim 8, wherein the internal upper surface is smoother than the internal lower surface.

10. The apparatus according to claim 8, further comprising a ceramic sleeve that circumferentially surrounds a distal portion of the optical fiber, at least a portion of the ceramic sleeve being disposed within the tissue-cutting element.

11. The apparatus according to claim 10, further comprising an adhesive, the adhesive forming a watertight seal between:

the ceramic sleeve and the tissue-cutting element, and the optical fiber and the ceramic sleeve.

12. The apparatus according to claim 1, wherein the internal surface of the hollow cavity is a reflective coating.

13. The apparatus according to claim 1, wherein:

the internal upper surface of the hollow cavity has a high reflectivity, and the upper edge of the tissue-cutting element of the mechanical cutting blade forms a lower surface of the hollow cavity, the internal upper surface of the hollow cavity is shaped so as to reflect the laser energy in a direction that is toward both the upper and lower edges of the tissue-cutting element.

14. The apparatus according to claim 13, wherein the mechanical cutting blade is configured such that the lower surface of the hollow cavity reflects no more than 30 percent of the laser energy that reaches the lower surface of the hollow cavity.

15. The apparatus according to claim 13, wherein the mechanical cutting blade is configured such that, for a same amount of laser energy that reaches the internal upper surface of the hollow cavity and the lower surface of the hollow cavity, the internal upper surface of the hollow cavity reflects at least two times as much of the laser energy.

16. The apparatus according to claim 13, wherein the mechanical cutting blade is configured such that the internal upper surface of the hollow cavity reflects at least 85 percent of the laser energy that reaches the internal upper surface.

17. The apparatus according to claim 13, wherein the internal upper surface of the hollow cavity has a reflective coating.

18. The apparatus according to claim 13, further comprising a pivot, wherein the mechanical cutting blade is configured to pivot toward the tissue-stabilizing base around the pivot, and wherein a distal end of the optical fiber is disposed within the pivot.

19. The apparatus according to claim 18, wherein:

the mechanical cutting element has at least two positions as it pivots toward the tissue-stabilizing base, wherein (a) in a first one of the at least two positions the laser energy is reflected toward a first location along the upper edge of the tissue-cutting element, and (b) in a second one of the at least two positions the laser energy is reflected toward a second location along the upper edge of the tissue-cutting element, distal to the first location.

20. The apparatus according to claim 19, wherein:

the optical fiber is positioned so as to emit the laser energy into the hollow cavity in a direction that is parallel to a central longitudinal axis of the elongate shaft, and the mechanical cutting blade is configured such that as the mechanical cutting blade pivots, the distal end of the optical fiber remains parallel to the central longitudinal axis of the elongate shaft.

* * * * *